(12) United States Patent
Weston et al.

(10) Patent No.: US 8,323,264 B2
(45) Date of Patent: Dec. 4, 2012

(54) AUXILIARY POWERED NEGATIVE PRESSURE WOUND THERAPY APPARATUSES AND METHODS

(75) Inventors: Richard Scott Weston, Carlsbad, CA (US); Farhad Bybordi, Pompano Beach, FL (US); Edward Yerbury Hartwell, Hull (GB); Kristian David Hall, Hull (GB)

(73) Assignees: BlueSky Medical Group, Inc., Memphis, TN (US); Smith & Nephew PLC, London (GB)

( * ) Notice: Subject to any disclaimer, the term of this patent is extended or adjusted under 35 U.S.C. 154(b) by 556 days.

(21) Appl. No.: 12/444,841

(22) PCT Filed: Oct. 17, 2007

(86) PCT No.: PCT/US2007/081687
§ 371 (c)(1),
(2), (4) Date: Apr. 8, 2009

(87) PCT Pub. No.: WO2008/049029
PCT Pub. Date: Apr. 24, 2008

(65) Prior Publication Data
US 2010/0042074 A1 Feb. 18, 2010

Related U.S. Application Data

(60) Provisional application No. 60/852,369, filed on Oct. 17, 2006.

(51) Int. Cl.
*A61M 27/00* (2006.01)
(52) U.S. Cl. ............... 604/543; 604/8; 604/9; 604/249; 604/288.03; 604/537; 604/540; 604/544; 600/29; 600/30; 600/31; 623/23.64; 623/23.65; 623/23.68; 623/23.7

(58) Field of Classification Search .................. 604/537, 604/540, 543, 544
See application file for complete search history.

(56) References Cited

U.S. PATENT DOCUMENTS
3,841,331 A 10/1974 Wilder et al.
(Continued)

FOREIGN PATENT DOCUMENTS
CA 2198243 A1 2/1996
(Continued)

OTHER PUBLICATIONS

Bagautdinov, "Variant of External Vacuum Aspiration in the Treatment of Purulent Diseases of Soft Tissues," Current Problems in Modern Clinical Surgery, 1986, 4 pages.

(Continued)

*Primary Examiner* — Tatyana Zalukaeva
*Assistant Examiner* — Ilya Treyger
(74) *Attorney, Agent, or Firm* — Knobbe, Martens, Olson & Bear LLP

(57) ABSTRACT

A negative pressure wound therapy apparatus that can include a wound dressing, a fluid collection device, a vacuum pump comprising a pump motor, and tubing can be powered by auxiliary power sources such as high efficiency batteries, photovoltaic panels or cells, fuel cells, combustion generators, human powered generators, or other mechanical, electrical, or chemical power sources such as hand operated dynamos or wound springs, or any combination of the foregoing. Additionally, the apparatus can include a high efficiency pressure controller for controlling the output of the vacuum pump. In some embodiments, the pressure controller can control the pump without using a processor, and can have other features such as an intermittent delay function and an anti-stall mechanism to reduce the energy consumption of the apparatus.

17 Claims, 25 Drawing Sheets

U.S. PATENT DOCUMENTS

| | | | |
|---|---|---|---|
| 4,102,342 A | 7/1978 | Akiyama et al. |
| 4,316,466 A | 2/1982 | Babb |
| 4,382,441 A | 5/1983 | Svedman |
| 4,404,924 A | 9/1983 | Goldberg et al. |
| 4,648,870 A | 3/1987 | Goldberg et al. |
| 4,740,202 A | 4/1988 | Stacey et al. |
| 4,795,448 A | 1/1989 | Stacey |
| 4,969,880 A | 11/1990 | Zamierowski |
| 4,979,944 A | 12/1990 | Luzsicza |
| 4,981,474 A | 1/1991 | Bopp et al. |
| 5,071,409 A | 12/1991 | Rosenberg |
| 5,429,601 A | 7/1995 | Conley et al. |
| 5,449,347 A | 9/1995 | Preen et al. |
| 5,549,584 A | 8/1996 | Gross |
| 5,636,643 A | 6/1997 | Argenta et al. |
| 5,637,093 A | 6/1997 | Hyman et al. |
| 5,645,081 A | 7/1997 | Argenta et al. |
| 5,786,682 A | 7/1998 | Aiken et al. |
| 5,928,265 A | 7/1999 | Fleischmann |
| 6,110,197 A | 8/2000 | Augustine et al. |
| 6,135,116 A | 10/2000 | Vogel et al. |
| 6,368,311 B1 | 4/2002 | Valerio et al. |
| 6,458,109 B1 | 10/2002 | Henley et al. |
| 6,648,862 B2 | 11/2003 | Watson |
| 7,004,915 B2 | 2/2006 | Boynton et al. |
| 7,108,683 B2 | 9/2006 | Zamierowski |
| 7,128,735 B2 | 10/2006 | Weston |
| 7,160,273 B2 | 1/2007 | Greter et al. |
| 7,216,651 B2 | 5/2007 | Argenta et al. |
| 7,611,500 B1 | 11/2009 | Lina et al. |
| 7,708,724 B2 | 5/2010 | Weston |
| 7,776,028 B2 | 8/2010 | Miller et al. |
| 7,790,945 B1 | 9/2010 | Watson, Jr. |
| 7,811,269 B2 | 10/2010 | Boynton et al. |
| 7,846,141 B2 | 12/2010 | Weston |
| 7,909,805 B2 | 3/2011 | Weston |
| 7,998,125 B2 | 8/2011 | Weston |
| 8,062,272 B2 | 11/2011 | Weston |
| 8,100,887 B2 | 1/2012 | Weston |
| 2002/0161346 A1 | 10/2002 | Lockwood et al. |
| 2002/0183702 A1 | 12/2002 | Henley et al. |
| 2002/0198503 A1 | 12/2002 | Risk et al. |
| 2003/0014022 A1 | 1/2003 | Lockwood et al. |
| 2003/0040687 A1 | 2/2003 | Boynton et al. |
| 2003/0097100 A1 | 5/2003 | Watson |
| 2004/0064132 A1 | 4/2004 | Boehringer et al. |
| 2004/0073151 A1 | 4/2004 | Weston |
| 2005/0203452 A1 | 9/2005 | Weston |
| 2005/0222527 A1 | 10/2005 | Miller et al. |
| 2005/0222528 A1 | 10/2005 | Weston |
| 2005/0222544 A1 | 10/2005 | Weston |
| 2005/0261615 A1 | 11/2005 | Weston |
| 2005/0261642 A1 | 11/2005 | Weston |
| 2005/0269374 A1 | 12/2005 | Koerner et al. |
| 2006/0025727 A1 | 2/2006 | Boehringer et al. |
| 2007/0014837 A1 | 1/2007 | Johnson et al. |
| 2007/0055209 A1 | 3/2007 | Patel et al. |
| 2007/0118096 A1 | 5/2007 | Smith et al. |
| 2007/0239139 A1 | 10/2007 | Weston et al. |
| 2008/0071234 A1 | 3/2008 | Kelch et al. |
| 2008/0200906 A1 | 8/2008 | Sanders et al. |
| 2008/0234641 A1 | 9/2008 | Locke et al. |
| 2009/0163882 A1 | 6/2009 | Koch et al. |
| 2009/0234260 A1 | 9/2009 | Coward et al. |
| 2009/0254066 A1 | 10/2009 | Heaton et al. |
| 2011/0022013 A1 | 1/2011 | Boynton et al. |

FOREIGN PATENT DOCUMENTS

| | | | |
|---|---|---|---|
| CA | 2237606 A1 | | 5/1997 |
| CA | 2551340 A1 | | 5/1997 |
| CA | 2458285 A1 | | 3/2003 |
| DE | 19517699 | * | 5/1995 |
| DE | 19517699 A1 | | 11/1996 |
| DE | 10 2005 014420 A1 | | 9/2006 |
| EP | 0 194 198 A | | 9/1986 |
| EP | 1 088 569 A | | 4/2001 |
| GB | 2047438 A | | 3/1980 |
| GB | 2195255 A | | 4/1988 |
| GB | 2235877 A | | 9/1989 |
| GB | 2342584 A | | 4/2000 |
| WO | WO 96/05873 | | 2/1996 |
| WO | WO 00/21586 | | 4/2000 |
| WO | WO 01/37922 | * | 5/2001 |
| WO | WO 01/37922 A2 | | 5/2001 |
| WO | WO 03/005943 | | 1/2003 |
| WO | 2006/052745 A | | 5/2006 |
| WO | WO 2006/052745 | * | 5/2006 |
| WO | WO 2007/019038 A | | 2/2007 |
| WO | WO 2007/030599 | | 3/2007 |
| WO | WO 2007/088530 | | 8/2008 |
| WO | WO 2008/112304 A1 | | 9/2008 |
| WO | WO 2008/131896 A1 | | 11/2008 |

OTHER PUBLICATIONS

International Search Report and Written Opinion for International Application No. PCT/US07/081687, dated Jul. 4, 2008, in 20 pages.

International Preliminary Report on Patentability for International Application No. PCT/US07/081687, dated Apr. 30, 2009, in 13 pages.

Jeter, Katherine F. ET, Managing Draining Wounds and Fistulae: New and Established Methods, Chronic Wound Care, Chapter 27, pp. 240-246.

Nursing75, Wound Suction: Better Drainage with Fewer Problems, Oct., 52-53.

Chinese Office Action for Chinese Application No. 200780046626.4, dated May 31, 2011 in 12 pages.

Info V.A.C. User Manual—KCI—Dec. 2006 (76 pages).

Japanese Office Action for Japanese Application No. 2009-533512 dated Jun. 5, 2012 in 7 pages.

US Medco Healthcare, Healing through Technology, HYPOwound Therapy System, from website http://www.usmedco.net Downloaded from internet Apr. 18, 2006.

* cited by examiner

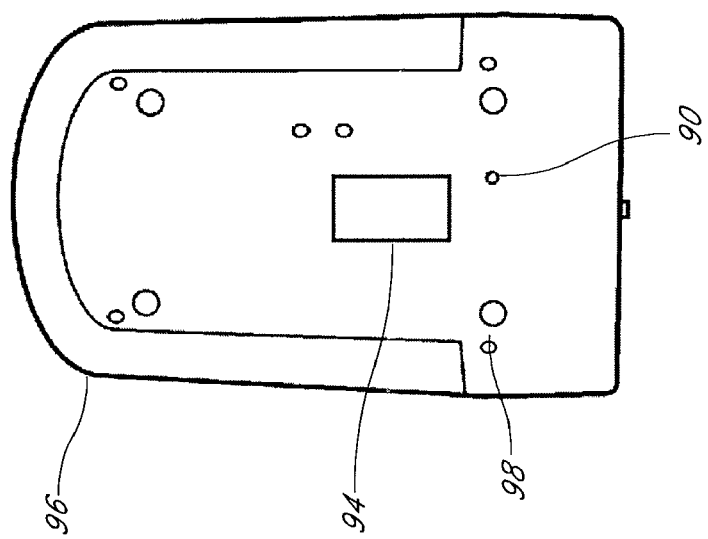
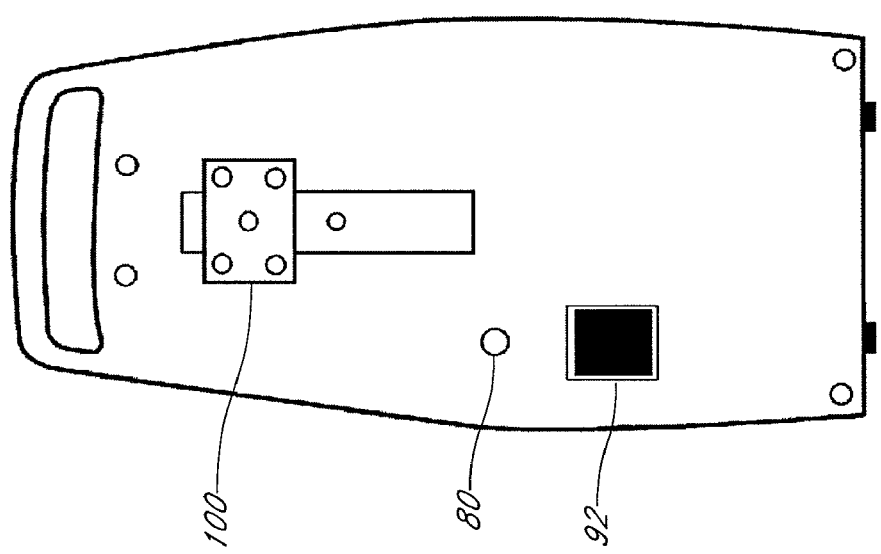

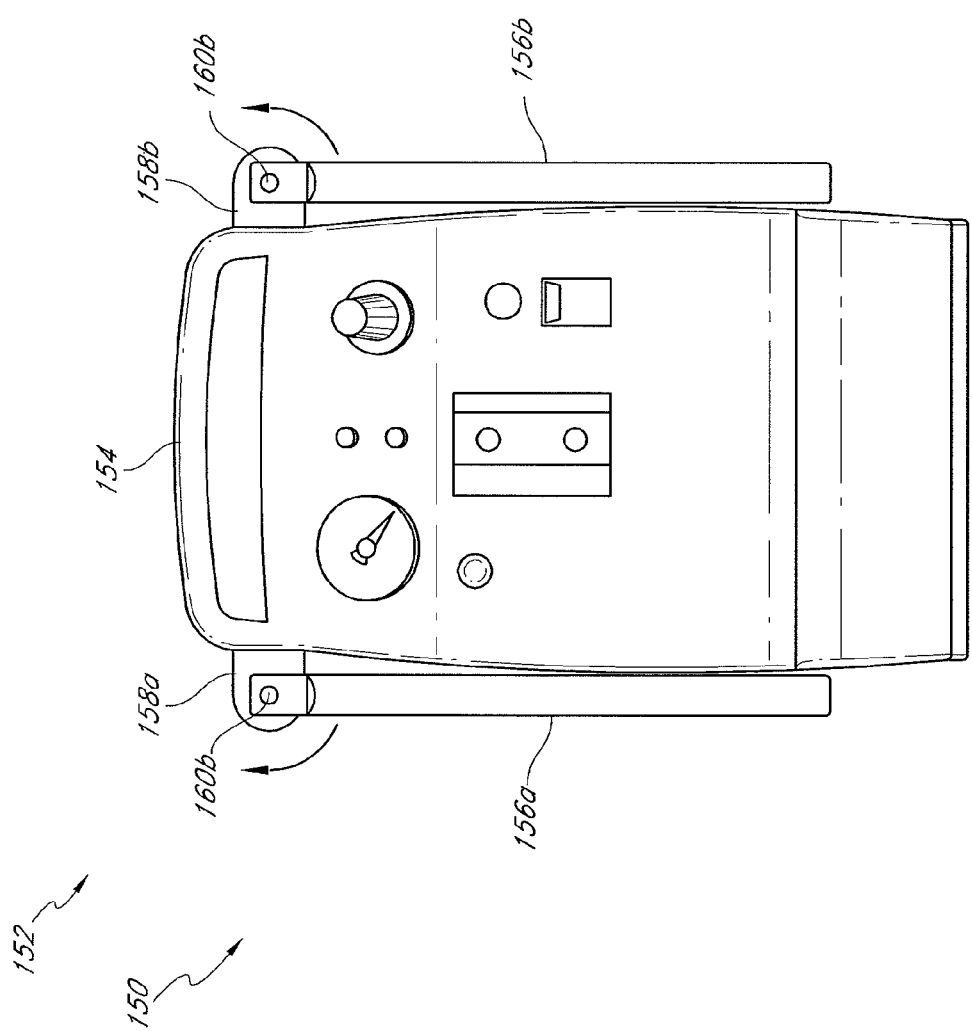

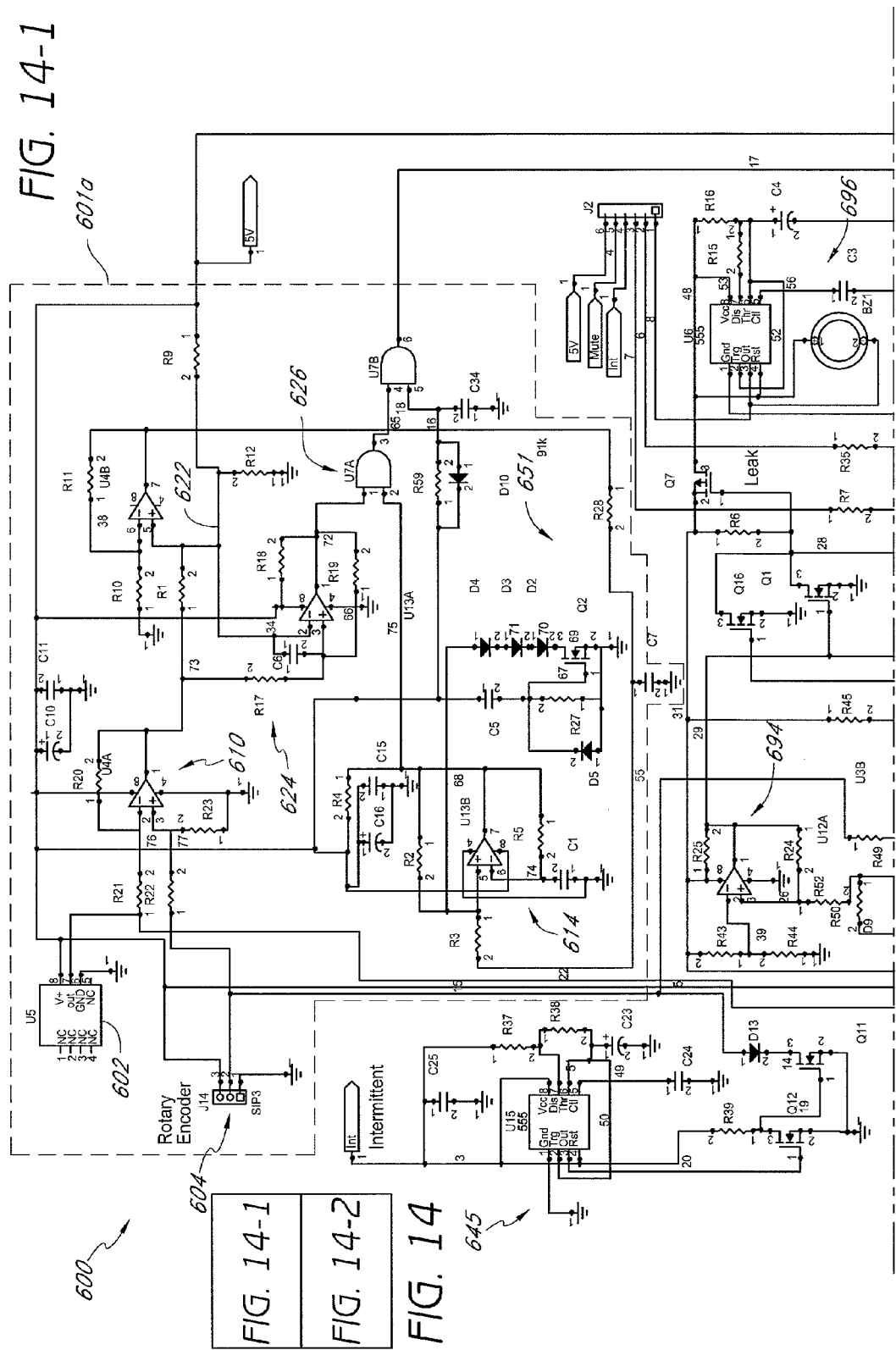

AUXILIARY POWERED NEGATIVE PRESSURE WOUND THERAPY APPARATUSES AND METHODS

RELATED APPLICATIONS

This application is a U.S. National Phase of International Application No. PCT/US2007/081687, filed Oct. 17, 2007, designating the United States and published on Apr. 24, 2008 as WO 2008/049029, and which claims priority to U.S. Provisional Application No. 60/852,369, filed Oct. 17 2006. The contents of these applications are incorporated herein by reference in their entirety

BACKGROUND

1. Technical Field

The present disclosure relates in certain embodiments to apparatuses and methods for treating a wound by applying reduced or negative pressure to the wound. In this context, the term "wound" is to be interpreted broadly to include any body part of a patient that may be treated using reduced pressure. In particular, certain embodiments of the present disclosure relate to the use of an auxiliary power source in a negative pressure wound therapy apparatus.

2. Description of the Related Art

The treatment of open or chronic wounds that are too large to spontaneously close or otherwise fail to heal has long been a troublesome area of medical practice. Closure of an open wound requires inward migration of surrounding epithelial and subcutaneous tissue. Some wounds, however, are sufficiently large or infected that they are unable to heal spontaneously. In such instances, a zone of stasis in which localized edema restricts the flow of blood to the epithelial and subcutaneous tissue forms near the surface of the wound. Without sufficient blood flow, the wound is unable to successfully fight bacterial infection and is accordingly unable to close spontaneously.

An initial stage of wound healing is characterized by the formation of granulation tissue which is a matrix of collagen, fibronectin, and hyaluronic acid carrying macrophages, fibroblasts, and neovasculature that forms the basis for subsequent epithelialization of the wound. Infection and poor vascularization hinder the formation of granulation tissue within wounded tissue, thereby inhibiting wound healing. It therefore becomes desirable to provide a technique for increasing blood circulation within wounded tissue to promote spontaneous healing and to reduce infection.

Another problem encountered during the treatment of wounds is the selection of an appropriate technique for wound closure during the healing process. Sutures are often used to apply force to adjacent viable tissue in order to induce the edges of a wound to migrate together and heal. However, sutures apply a closure force to only a very small percentage of the area surrounding a wound. When there is scarring, edema, or insufficient tissue, the tension produced by the sutures can become great causing excessive pressure to be exerted by the sutures upon the tissue adjacent to each suture. As a result, the adjacent tissue often becomes ischemic thereby rendering suturing of large wounds counterproductive. If the quantity or size of the sutures is increased to reduce the tension required of any single suture, the quantity of foreign material within the wound is concomitantly increased and the wound is more apt to become infected. Additionally, the size or type of a particular wound may prevent the use of sutures to promote wound closure. It therefore becomes desirable to provide an apparatus and method for closing a large wound that distributes a closure force evenly about the periphery of the wound.

Wounds resulting from ischemia, or lack of blood flow, are also often difficult to heal since decreased blood flow to a wound may inhibit normal immune reaction to fight infection. Patients that are bedridden or otherwise non-ambulatory are susceptible to such ischemic wounds as decubitus ulcers or pressure sores. Decubitus ulcers form as a result of constant compression of the skin surface and underlying tissue thus restricting circulation. Since the patient is often unable to feel the wound or to move sufficiently to relieve the pressure, such wounds can become self-perpetuating. Although it is common to treat such wounds with flaps, the conditions that initially caused the wound may also work against successful flap attachment. Wheelchair-bound paraplegics, for example, must still remain seated after treatment of pelvic pressure sores. It therefore becomes desirable to provide a treatment procedure for ischemic wounds that can be conducted in situ upon an immobile or partially mobile patient.

Other types of wounds in which ischemia leads to progressive deterioration include partial thickness burns. A partial thickness burn is a burn in which the cell death due to thermal trauma does not extend below the deepest epidermal structures such as hair follicles, sweat glands, or sebaceous glands. The progression of partial thickness burns to deeper burns is a major problem in burn therapy. The ability to control or diminish the depth of burns greatly enhances the prognosis for burn patients and decreases morbidity resulting from burns. Partial thickness burns are formed of a zone of coagulation, which encompasses tissue killed by thermal injury, and a zone of stasis. The zone of stasis is a layer of tissue immediately beneath the zone of coagulation. Cells within the zone of stasis are viable, but the blood flow is static because of collapse of vascular structures due to localized edema. Unless blood flow is re-established within the zone of stasis soon after injury, the tissue within the zone of stasis also dies. The death of tissue within the zone of stasis is caused by lack of oxygen and nutrients, reperfusion injury (re-establishment of blood flow after prolonged ischemia), and decreased migration of white blood cells to the zone resulting in bacterial proliferation. Again, it becomes desirable to provide a technique for treating burn wounds by enhancing blood circulation to the wounded tissue to inhibit burn penetration.

There exist various apparatuses utilizing reduced pressure for treatment of these types of wounds. However, the existing apparatuses are often limited to locally available power sources, and do not provide adequate means to utilize the apparatuses in other environments.

SUMMARY OF SOME EMBODIMENTS

Certain embodiments of the present disclosure relate to negative pressure wound therapy ("NPWT"), also known as suction therapy or vacuum therapy, used in a wound healing environment specifically where there is a strong need to use the system in an area where there is a need for auxiliary or backup power source beyond just alternating current or AC or direct power source from electric power source. This concept can be extended to other medical devices as well. As used herein, the phrase auxiliary power source is used to represent any source of power other than an alternating current (AC) power source.

Embodiments of the present invention address an increased need for usage of negative pressure wound therapy systems in more contemporary conditions such as mobile patients or semi-mobile patients, and in areas where there is a strong need for a usage of auxiliary power systems. Direct current DC operations, battery powers, solar powers, fusions, solar cells or any combination of the above make it possible for patients to be under therapy nonstop while they are temporarily immobile or completely mobile.

As a result of these innovations in the auxiliary power source usage, patients may be able to complete a course of therapy faster than if they were confined to a caring facility which has access only to AC power sources for negative pressure wound therapy. Furthermore, by employing the auxiliary or backup power source, patients will be able to resume a more normal and functional lifestyle which is more in tune with their day to day routines.

Another benefit of auxiliary powered NPWT apparatuses is the ability to provide NPWT sources in remote areas where there is either no AC power available or the area is dangerous and hazardous to the safety of these patients, i.e., battle fronts or battle grounds in warfare situations which require an urgent, critical usage of auxiliary power to run a negative therapy pressure therapy system. Another benefit of auxiliary powered NPWT apparatuses is the ability to provide NPWT in areas without a reliable supply of electricity. These conditions are ideal for NPWT apparatuses having auxiliary power that can sustain the NPWT apparatus for several days or longer. Part of the innovative design of certain embodiments of the present disclosure is to recognize and provide for these needs.

The embodiments disclosed herein can provide an auxiliary source of power to an NPWT apparatus coupled with a high efficiency electrical circuit to conserve the energy supply to sustain such an apparatus for several days or longer. This would in turn create a brand new concept of a long life product used in suction applications or other medical applications specifically related to NPWT.

Certain embodiments described herein are directed to systems, methods and apparatuses for wound therapy. However, it will be appreciated that the systems, methods and apparatuses may have application to other fields. In certain preferred embodiments, the wounds being treated may include, but are not limited to, acute and chronic wounds, orthopedic trauma wounds, and post-Cesarean wounds, to name a few.

In some embodiments, such wounds are treated using an NPWT apparatus preferably comprising a wound dressing, a fluid collection device, a vacuum pump comprising a pump motor, one or more conduits, an auxiliary power module, and a power controller in electrical communication with at least the auxiliary power module and the vacuum pump. In some embodiments, the conduits are preferably configured to at least channel a flow of fluid between the wound dressing, the fluid collection device, and the pump. In some embodiments, the auxiliary power module can be configured to provide a first electrical current to the power controller, and the power controller can be configured to at least provide a second electrical current to at least the vacuum pump based at least on the first electrical current and the energy requirements of the vacuum pump.

In some embodiments, the auxiliary power module of the NPWT apparatus described herein can be a photovoltaic panel. In some embodiments, the auxiliary power module of the NPWT apparatus described herein can be a fuel cell. In some embodiments, the auxiliary power module of the NPWT apparatus described herein can be a generator. In some embodiments, the auxiliary power module of the NPWT apparatus described herein can be human powered. In some embodiments, the auxiliary power module of the NPWT apparatus described herein can be combustion powered. In some embodiments, the auxiliary power module of the NPWT apparatus described herein can be a battery. In some embodiments, the auxiliary power module of the NPWT apparatus described herein can be a mechanical accumulator. In some embodiments, the power controller of the NPWT apparatus described herein can be further configured to accept an input of alternating current electricity.

In some embodiments, the NPWT apparatus described herein can further comprise a battery module in electrical communication with the power controller and configured to have an electrical input and an electrical output. In some embodiments, the power controller can be further configured such that the second electrical current provided to at least the vacuum pump can comprise the first electrical current from the auxiliary power module, or the electrical output from the battery module, or the first electrical current from the auxiliary power module and the electrical output from the battery module, depending on a magnitude of the first electrical current and an energy need from at least the vacuum pump. In some embodiments, the power controller can be further configured to provide at least a portion of the second electrical current to the battery so as to charge the battery when the magnitude of the first electrical current is greater than the energy need from at least the vacuum pump.

In some embodiments, the NPWT apparatus described herein can further comprise a pressure sensor and a control circuit, wherein the power controller can be further configured to provide a third electrical current to the control circuit, and the pressure sensor can be configured to measure a pressure in one or more of the one or more conduits and to generate a pressure sensor voltage reflecting pressure in one or more of the one or more conduits, and the control circuit can be configured to control a pressure in the one or more conduits without using a processor, based at least on the pressure sensor voltage.

In some embodiments, an NPWT apparatus comprising a wound dressing, a pressure unit, a conduit, and a drive unit is provided. In some embodiments, the drive unit can be in communication with the piston rod and can be configured to move at least the piston rod so as to cause at least the piston to reciprocate within the bore when the drive unit is driven by a source of motive power, such that a portion of fluid within the wound dressing can be caused to be drawn out of the wound dressing. In some embodiments, the pressure unit can comprise a bore, a piston rod, and a piston slidingly received within the bore and in communication with a first portion of the piston rod. In some embodiments, the conduit can be configured to channel fluid between at least the wound dressing and the pressure unit.

In some embodiments, the source of motive power of the NPWT apparatus described herein comprises a wound spring. In some embodiments, the source of motive power of the NPWT apparatus described herein comprises an electric motor. In some embodiments, the source of motive power of the NPWT apparatus described herein comprises an internal combustion motor. In some embodiments, the source of motive power of the NPWT apparatus described herein comprises a human operated dynamo.

In some embodiments, the NPWT apparatus described further comprises a control unit and a pressure sensor, the pressure sensor being configured to measure a pressure within the wound dressing and to provide a pressure input signal to the control unit, the control unit being configured to stop the motion of the drive unit when the pressure input signal reaches a predetermined value. In some embodiments, the NPWT apparatus described further comprises a compressor and an accumulator, the compressor being configured to pressurize the accumulator with pressurized air, and the accumulator being configured to supply the pressurized air within the accumulator to the drive unit, the drive unit being a pneumatic drive unit configured to move in response to a supply of pressurized air.

In some embodiments, the NPWT apparatus described herein further comprises a control unit and a pressure sensor, the pressure sensor being configured to measure a pressure within the wound dressing and to provide a pressure input signal to the control unit, wherein the control unit can be configured to control an amount of the pressurized air that is supplied to the drive unit based on the value of the pressure input signal.

In some embodiments, the NPWT apparatus described herein further comprises a control unit and a pressure sensor, the pressure sensor being configured to measure a pressure within the wound dressing and to provide a pressure input signal to the control unit, wherein the control unit can be configured to stop the supply of air to the drive unit when the value of the pressure input signal can be at least approximately equal to a predetermined value.

In some embodiments, a method of providing an auxiliary source of power to a pump for NPWT is provided. In some embodiments, the method comprises at least the steps of providing a power controller and an auxiliary power module and powering the pump with the auxiliary power module. In some embodiments, the auxiliary power module can be configured to provide an input of electrical current to the power controller, and the power controller can be in electrical communication with at least the auxiliary power module and the vacuum pump. In some embodiments, the power controller can be configured to provide an output electrical current to at least the vacuum pump based at least on the input of electrical current and the energy needs of the vacuum pump.

In some embodiments, a method for treating a wound is provided, comprising at least the steps of providing at least a wound dressing, a fluid collection device, a vacuum pump, one or more conduits, providing a power controller and an auxiliary power module, and controlling a pump motor to provide a negative pressure to the wound dressing. In some embodiments, one or more of the conduits can be configured to at least channel a flow of fluid between the wound dressing, the fluid collection canister, and the pump. In some embodiments, the auxiliary power module can be configured to provide an input of electrical current to the power controller, and the power controller can be in electrical communication with at least the auxiliary power module and the vacuum pump, and configured to provide an output electrical current to at least the vacuum pump based at least on the input of electrical current and the energy needs of the vacuum pump. In some embodiments, the pump motor can be powered by the auxiliary power module.

In some embodiments, the auxiliary power module of the method described herein can be a photovoltaic panel. In some embodiments, the auxiliary power module of the method described herein can be a fuel cell. In some embodiments, the auxiliary power module of the method described herein can be a generator that, in some embodiments, can be human powered or combustion powered. In some embodiments, the auxiliary power module of the method described herein can be a battery. In some embodiments, the auxiliary power module of the method described herein can be a mechanical accumulator.

In some embodiments, an NPWT apparatus is provided, comprising a vacuum pump and an auxiliary power module suitable for powering the pump motor when the pump is not connected to an AC power source. In some embodiments, the vacuum pump can comprise a pump motor. In some embodiments, the pump can be configured to be connected to an AC power source and an auxiliary power source. In some embodiments, the NPWT apparatus described herein can further comprise a conduit for providing negative pressure to a wound location. In some embodiments, the NPWT apparatus described herein can further comprise a wound dressing.

In some embodiments, the auxiliary power module of the NPWT apparatus described herein can be a photovoltaic panel. In some embodiments, the auxiliary power module of the NPWT apparatus described herein can be a fuel cell. In some embodiments, the auxiliary power module of the NPWT apparatus described herein can be a generator. In some embodiments, the auxiliary power module of the NPWT apparatus described herein can be human powered. In some embodiments, the auxiliary power module of the NPWT apparatus described herein can be combustion powered. In some embodiments, the auxiliary power module of the NPWT apparatus described herein can be a battery. In some embodiments, the auxiliary power module of the NPWT apparatus described herein can be a mechanical accumulator. In some embodiments, the power controller of the NPWT apparatus described herein can be further configured to accept an input of alternating current electricity.

BRIEF DESCRIPTION OF THE DRAWINGS

These and other features, aspects and advantages will now be described in connection with certain embodiments, in reference to the accompanying drawings. The illustrated embodiments, however, are merely examples and are not intended to be limiting. The following are brief descriptions of the drawings.

FIG. 3B is a planar view of the back side of an embodiment of the enclosure illustrated in FIG. 3A.

FIG. 3C is a planar view of the bottom side of an embodiment of the enclosure illustrated in FIG. 3A.

FIG. 7A is a front view of another embodiment of a negative pressure wound therapy apparatus, showing each of the two embodiments of the photovoltaic panel in a retracted position.

DETAILED DESCRIPTION OF THE PREFERRED EMBODIMENTS

The following detailed description is now directed to certain specific embodiments of the disclosure. In this description, reference is made to the drawings wherein like parts are designated with like numerals throughout the description and the drawings.

Preferred embodiments described herein relate to wound therapy. The term "wound" as used herein, in addition to having its broad ordinary meaning, includes any body part of a patient that may be treated using reduced pressure. Wounds include, but are not limited to, open wounds, pressure sores, ulcers and burns. Treatment of such wounds can be performed using negative pressure wound therapy, wherein a reduced or negative pressure can be applied to the wound to facilitate and promote healing of the wound. Additional descriptions of devices, methods, and systems that may be used for wound therapy may be found in U.S. Patent Application Publication No. 2004/0073151 A1, U.S. Pat. No. 7,128,735, International Patent Application Publication No. WO 2004/037334, International Patent Application Publication No. WO 2005/105180, U.S. Patent Application Publication No. US 2006/0155260, International Patent Application Publication No. WO 2005/046760, and U.S. Patent Application Publication No. US 2007/0129707, the entirety of all of which are hereby incorporated by reference and made a part of the present disclosure. It will also be appreciated that the negative pressure systems and methods as described herein may be applied to other parts of the body, and are not necessarily limited to treatment of wounds.

Figure 1:
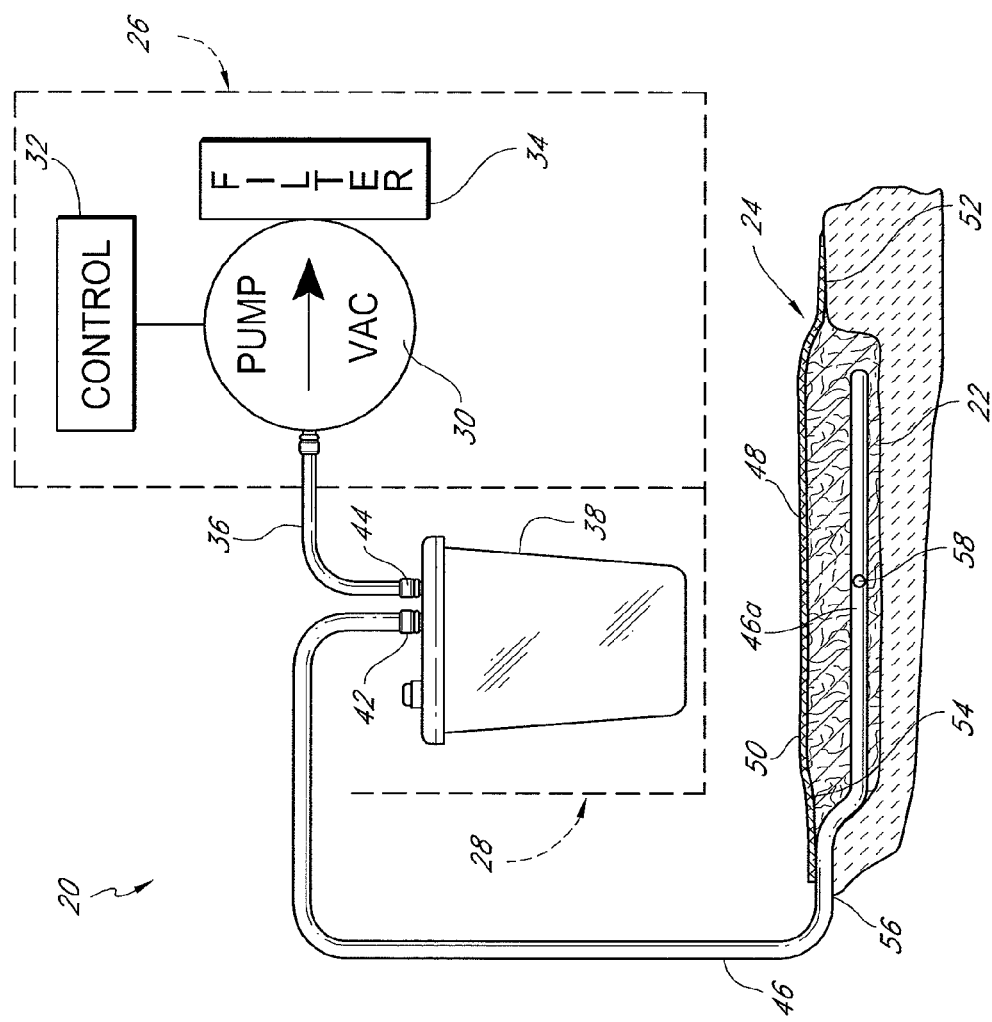
FIG. 1 is a schematic representation of an embodiment of negative pressure wound therapy apparatus.

FIG. 1 is a schematic representation of an embodiment of a negative pressure wound therapy ("NPWT") apparatus 20 according to an embodiment of the present disclosure. As described herein, the NPWT apparatus is preferably configured to treat a wound by application of reduced pressure to a wound site 22 (i.e., below atmospheric pressure) so as to provide suction to the wound site 22 in a controlled manner for a selected period of time.

As illustrated in FIG. 1, the NPWT apparatus 20 comprises a wound cover or wound dressing 24 for enclosing a wound site 22 and for providing a fluid-tight or gas-tight enclosure over the wound site 22 to effect treatment of a wound site 22 with reduced or negative pressure. Any wound cover or dressing presently known in the art or developed in the future can be configured to be integrated into the NPWT apparatus 20 described herein. For example, without limitation, the embodiments of the wound covering device set forth in U.S. Pat. No. 7,128,735, which disclosure is hereby incorporated by reference as if fully set forth herein, could be used in place of the flexible wound dressing 24 illustrated in FIG. 1.

For the purpose of creating suction within the wound dressing 24, the wound dressing 24 is connected to a vacuum system 26 to provide a source of suction or reduced pressure for the sealed wound dressing 24 at the wound site 22. Between the wound dressing 24 and the vacuum system 26 is a fluid collection system 28, for intercepting and retaining exudate that is aspirated from the wound site 22.

As shown in FIG. 1, the vacuum system 26, which produces a source of reduced pressure or suction that is supplied to the wound dressing 24, preferably comprises a vacuum pump 30, a vacuum system control device 32, a filter 34, and tubing 36 that connects the vacuum pump 30 to the collection system 28. Predetermined amounts of suction or reduced pressure are produced by the vacuum pump 30. The control device 32 preferably controls the vacuum pump 30 and may be any type suitable for NPWT typically used in the art.

A filter 34, such as micropore filter, is attached to the exhaust of the vacuum pump 30 to prevent potentially pathogenic microbes or aerosols from the wound site 22 from being vented to the atmosphere by the vacuum pump 30 when the fluid (meaning the air, gas, moisture, and/or exudate) within the wound dressing 24 is pumped out of the wound dressing 24. In some embodiments, not shown, the filter may preferably be positioned between the fluid collection system 28 and pump 30 along tubing 36 such that the pump may be protected from contaminated fluids. In some embodiments, the vacuum system 26 of the NPWT apparatus 20 can comprise two or more vacuum pumps 30 connected with tubing 36, preferably arranged in parallel. The additional pump 30 may ensure a higher level of safety and product quality by providing pump redundancy to prevent vacuum system failure in the event that a single pump fails, in addition to more efficiently providing increased suction.

The fluid collection system 28 is preferably interconnected between the suction vacuum pump 30 and the appliance 24 to remove and collect any exudate which may be aspirated from the wound site 22 by the wound dressing 24. The appliance 24 preferably functions to actively draw fluid or exudate from the wound site 22. Collection of exudate in a fluid collection system 28 between the vacuum pump 30 and the appliance 24 is preferred to prevent clogging of the vacuum pump 30.

As illustrated in FIGS. 1-2, 3D, and 3E, the fluid collection system 28 may be comprised of a fluid-impermeable collection container 38 and a shutoff mechanism 40. The container 38 may be of any size and shape suitable for intercepting and retaining a predetermined amount of exudate. Many examples of such containers are available in the relevant art. The container 38 illustrated preferably has a first port 42 and a second port 44 positioned on the top of the container 38. The first port 42 preferably enables suction to be applied to the wound dressing 24 through the tubing 46 and also enables exudate from the wound site 22 covered by wound dressing 24 to be drained into the container 38. The container 38 provides a means for containing and temporarily storing the collected exudate. A second port 44 is also provided on the top of the container 38 to enable the application of suction from the vacuum pump 30 to the container 38. As mentioned above, the second port 44 of the collection system 28 is connected to the vacuum pump 30 by a vacuum line 36. The collection system 28 is preferably sealed approximately gas-tight so that as to enable the suction vacuum pump 30 to supply suction to the appliance 24 through the collection system 28.

The fluid-impermeable wound cover 50 in the embodiment of the wound dressing 24 illustrated in FIG. 1 may be in the form of a flexible, adhesive, fluid impermeable polymer sheet for covering and enclosing the wound site 22, including an optional absorbable or non-bioabsorbable matrix 48 within it, and the surrounding normal skin 50 around the wound site 22. The matrix 48 may be any type typically used in the art, such as is described in U.S. Patent Application Publication No. US 2004/0073151 A1, which is incorporated by reference herein in its entirety. The wound cover 50 preferably includes an adhesive backing 54 which functions to seal the wound cover 50 to the normal skin 52 around the periphery of the wound site 22 so as to provide a generally gas-tight or fluid-tight enclosure over the wound site 22. The adhesive cover 40 preferably has sufficient adhesion to form a fluid-tight or gas-tight seal around the periphery of the wound site 22 and to hold the cover 50 in sealed contact with the skin 52 during the application of suction or reduced or negative pressure. The wound cover 50 also preferably provides a gas-tight seal around the tubing 46 at the feedthrough location 56 where the tubing 46 emerges from beneath the wound cover 50. The conduit or tube segment 46a embedded within the absorbable matrix 48 preferably has at least one side port 58 positioned within the interior of the absorbable matrix 48 to enable a substantially uniform application of reduced pressure throughout the enclosure.

Figure 2:
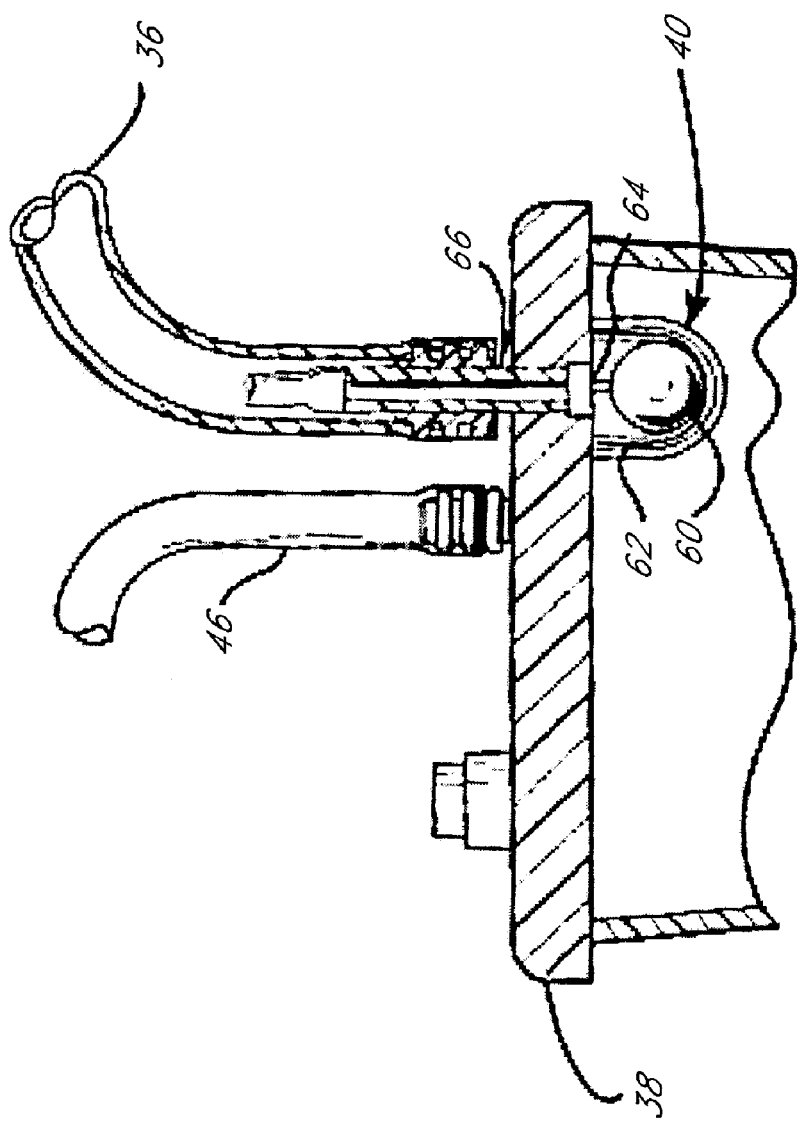
FIG. 2 is a section view of a portion of an embodiment of a collection device.

FIG. 2 is a section view of the collection system 28 of the NPWT apparatus 20 illustrated in FIG. 1. As previously stated, the vacuum system 26 and collection system 28 preferably include a shutoff mechanism 40 for halting or inhibiting the supply of the reduced pressure to the appliance 24 in the event that the exudate aspirated from the wound 22 exceeds a predetermined quantity. Interrupting the application of suction to the appliance 24 is desirable to prevent exsanguination in the unlikely event a blood vessel ruptures under the wound cover 50 during treatment. If, for example, a blood vessel ruptures in the vicinity of the wound 22, a shutoff mechanism may be useful to prevent the vacuum system 26 from aspirating any significant quantity of blood from the patient.

The shutoff mechanism 40 may be comprised of any means that enables the vacuum system 26 to halt the supply of reduced pressure to the wound cover 50 at any time that the volume of exudate from the wound 22 exceeds a predetermined amount. Such means may include mechanical switches, electrical switches operably connected to the vacuum system control device 32, optical, thermal or weight sensors operably connected to the vacuum system control device 32, and any other means that are currently known in the relevant art or are suitable for this function.

The shutoff mechanism 40, as illustrated in FIG. 2, is preferably a float valve assembly comprising a ball 60 which is held and suspended within a cage 62 positioned below a valve seat 64 disposed within the opening at the top of the container below the second port that will float upon the exudate and will be lifted against the valve seat 64 as the container fills with exudate. When the ball 60 is firmly seated against the valve seat 64, the float valve blocks the second port 66 and thereby shuts off the source of suction from the vacuum system 26. Other types of mechanisms may also be employed to detect the liquid level within the container 38 in order to arrest operation of the vacuum system 50.

Figure 3A:
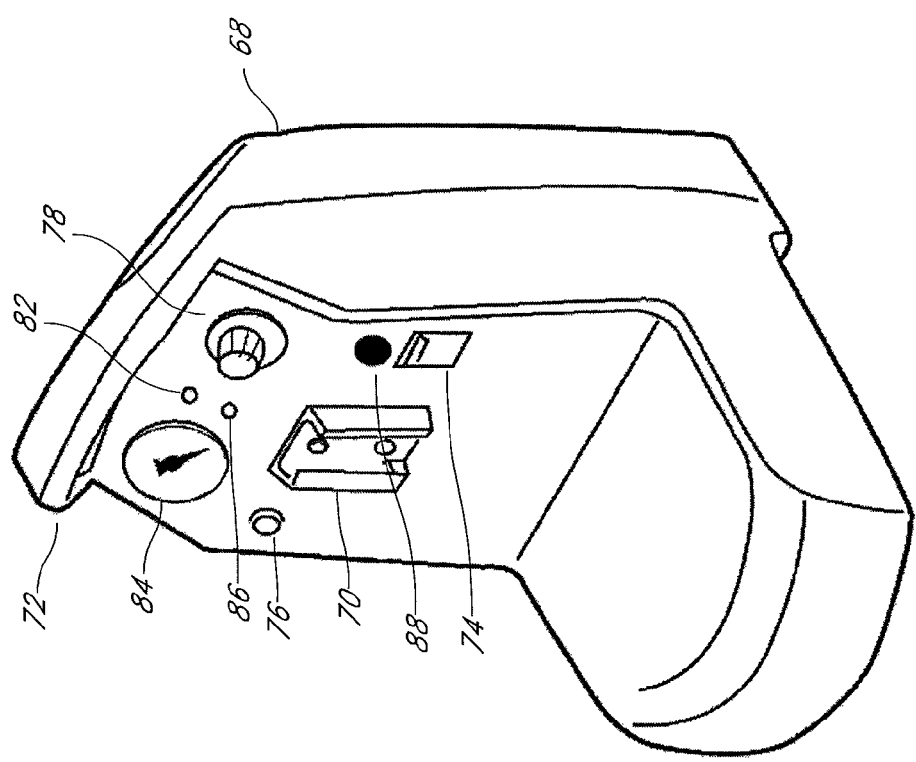
FIG. 3A is a perspective view of the outside of an embodiment of an enclosure for a negative pressure wound therapy apparatus.

FIG. 3A is a perspective view of an embodiment of the outside of a enclosure 68 for an NPWT apparatus, FIG. 3B is a planar view of the back side of the enclosure illustrated in FIG. 3A, and FIG. 3C is a planar view of the bottom side of the enclosure illustrated in FIG. 3A. The enclosure 68 illustrated in FIGS. 3A-3C can be used to enclose and/or support many of the components and features comprising some embodiments of the NPWT apparatus described herein. In the illustrated embodiment, the enclosure 68 preferably encloses and/or supports the fluid collection system and vacuum system, including but not limited to the vacuum pump, vacuum system control device, filter, and tubing that connects the vacuum pump to the collection system.

Additionally, as illustrated in FIGS. 3A-3C, the enclosure 68 preferably also supports or comprises a container adapter bracket 70, a handle 72, a power switch 74, a vacuum port 76, a pressure selector 78 which switches the pump configuration from a continuous to an intermittent output configuration, a 12 volt DC input 80, a low pressure LED light 82, a pressure/vacuum gauge 84, a low battery LED light 86, an alarm suppress button 88, an air exhaust outlet 90, an AC power inlet and fuse 92, a specification badge 94, a rolling stand connection 96, rubber feet 98, and a universal holder bracket 100.

The low pressure LED light 82 is preferably configured to warn the user of the NPWT apparatus when the vacuum level is low or there is a leak in the system. Pressing the alarm suppress button 88 will suppress the low pressure LED light 82 after it has been activated. The low battery LED light 86 is preferably configured to warn the user of the NPWT apparatus when the battery power level is low. The low battery LED light 86 may be accompanied by an audible warning noise or "chirp" when the battery power level is low. Pressing the alarm suppress button 88 will suppress the low battery LED light 86 and/or audible warning noise. The enclosure 68 also preferably includes a lithium ion rechargeable battery (not shown) that is recharged when an AC power supply is connected to the enclosure 68.

Figure 3E:
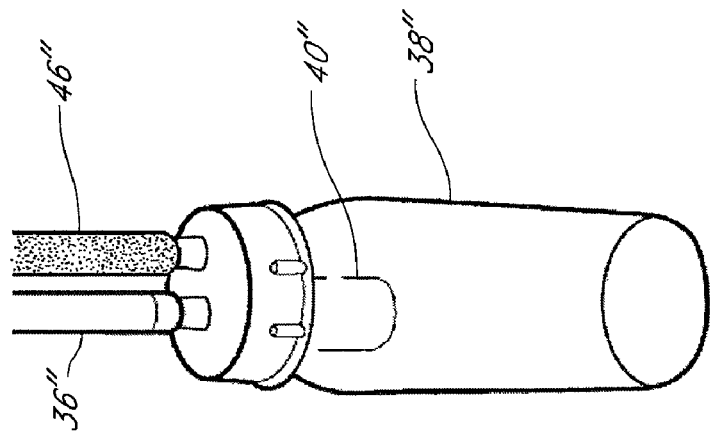
FIG. 3E is a perspective view of the outside of another embodiment of a fluid collection device.
Figure 3D:
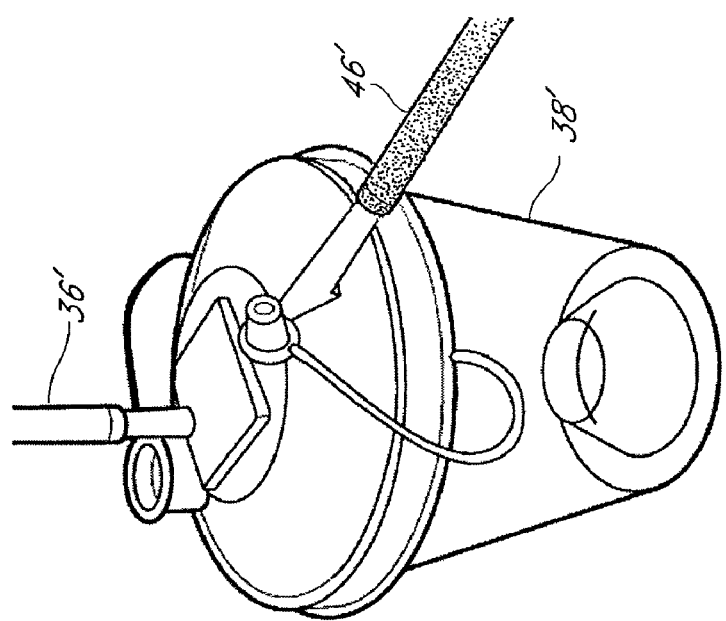
FIG. 3D is a perspective view of the outside of an embodiment of a fluid collection device.

FIG. 3D is a perspective view of the outside of another embodiment of a fluid collection container 38' that can be secured to the container adapter bracket 70 of the enclosure 68 described above. In the illustrated embodiment, the volume of the fluid collection container 38' is approximately 800 cubic centimeters. The fluid collection container 38' is preferably connected to the vacuum pump 30 by tubing 36', and to the wound dressing 24 through the tubing 46'. Additionally, the fluid collection container 38' illustrated in FIG. 3D preferably comprises a shutoff mechanism (not shown) to halt or inhibit the supply of the reduced or negative pressure to the appliance 24 in the event that the exudate aspirated from the wound 22 exceeds a predetermined quantity.

FIG. 3E is a perspective view of the outside of another embodiment of a fluid collection container 38" that can be secured to the container adapter bracket 70 of the enclosure 68 described above. In the illustrated embodiment, the volume of the fluid collection container 38" is approximately 250 cubic centimeters. The fluid collection container 38" is preferably connected to the vacuum pump 30 by tubing 36", and to the wound dressing 24 through the tubing 46". Additionally, the fluid collection container 38" illustrated in FIG. 3E preferably comprises a shutoff mechanism 40" to halt or inhibit the supply of the reduced or negative pressure to the appliance 24 in the event that the exudate aspirated from the wound 22 exceeds a predetermined quantity.

Figure 4:
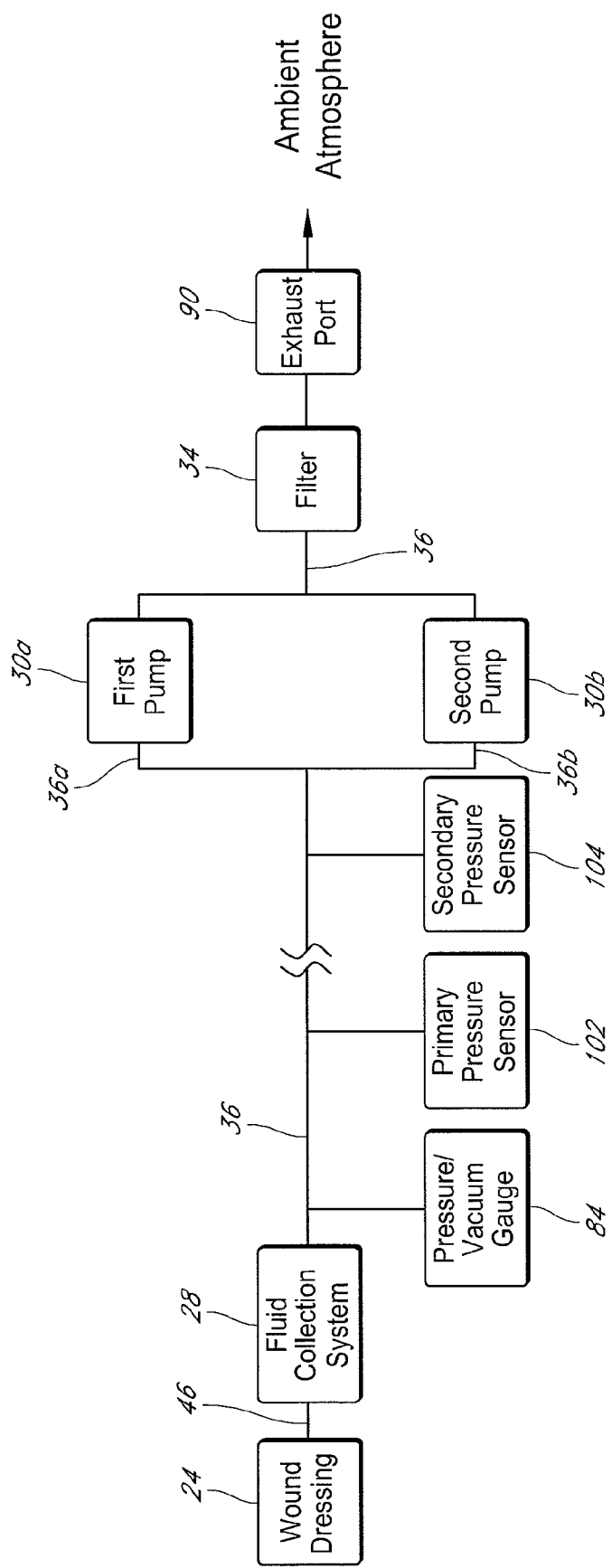
FIG. 4 is a schematic representation of an embodiment of a vacuum system.

FIG. 4 is a schematic representation of an embodiment of a vacuum system 26, illustrating the suction and exhaust circuits and the relative position of the components therein. In the illustrated embodiment, a first pump 30a and a second pump 30b are connected in parallel via tubing 36a, 36b, respectively, which are joined to tubing 36 using a standard tubing connector. The addition of the second pump 30b may ensure a higher level of safety and product quality by providing pump redundancy to prevent vacuum system failure in the event that a single pump fails, in addition to more efficiently providing increased suction. Tubing 36a, 36b then joins the outlet flow from the first and second pumps 30a, 30b together using a standard tubing connector, and channels the outlet flow through the filter 34 and then out through the exhaust port 90 to the ambient atmosphere.

In the illustrated embodiment, the vacuum system 26 preferably has a primary pressure sensor 102 and a secondary pressure sensor 104. As illustrated in FIG. 4, the primary pressure sensor 102 is located further upstream from the pumps 30a, 30b as compared to the secondary pressure sensor 104 (i.e., of the two pressure sensors 102, 104, the primary pressure sensor 102 is preferably located closer to the wound dressing 24 in the illustrated embodiment). Describing the components according to their preferred position in the illustrated embodiment relative to the pumps 30a, 30b, the secondary pressure sensor 104 is preferably positioned to read the pressure in the tubing 36 upstream of the pumps 30a, 30b. The secondary pressure sensor 104 detects the fluid pressure within the tubing 36 and is preferably configured to shut down the power to both pumps 30a, 30b when the pressure reading by the secondary pressure sensor 104 exceeds a predetermined threshold value. The pressure reading by the secondary pressure sensor 104 may exceed a predetermined threshold value when, for example, the shutoff mechanism 40 is activated. While just a single pressure sensor could be used to operate the NPWT apparatus 20, an additional pressure sensor allows for flow rate measurements to help detect leaks in the system and to activate a high flow rate alarm, among other reasons, as discussed below.

Positioned to read the pressure further upstream, e.g., in the direction of the fluid collection container 38 and the wound dressing 24, the primary pressure sensor 102 detects the pressure in the tubing between the secondary pressure sensor 104 and the fluid collection container 28. The primary pressure sensor 102 preferably provides instantaneous or near-instantaneous pressure values to the vacuum system control device 32 that is preferably used to control the vacuum pump 30. The primary pressure sensor 102 can also be configured to activate the circuitry of the low pressure alarm, e.g., the low pressure LED light 82, when the pressure detected by the primary pressure sensor 102 is lower than a predetermined value for a significant amount of time.

The primary pressure sensor 102 and/or the secondary pressure sensor 104 can be of any suitable configuration known in the art, such as, but not limited to, an ASDX series pressure transducer manufactured by Honeywell Sensing and Control. In some embodiments, the primary pressure sensor 102 and/or the secondary pressure sensor 104 are preferably located on the control board used to control an output of one or more pumps 30.

In some embodiments, the low pressure alarm is activated when the pressure detected by the primary pressure sensor 102 is lower than a predetermined value for approximately forty seconds or longer, or for approximately fifty seconds or longer, or for approximately sixty seconds or longer, or for approximately seventy seconds or longer, or for approximately eighty seconds or longer, or for approximately one hundred seconds or longer, or for approximately one hundred twenty seconds or longer, or for approximately one hundred thirty seconds or longer.

In some embodiments, pressure sensors 102, 104 can be slightly apart from each other or can be adjacent to each other. However, in other embodiments, such as the illustrated embodiment, the sensors 102, 104 can be a greater distance apart from each other. In addition, a flow restrictor (not shown) or the like can be positioned between the sensors 102, 104 to restrict air flow in the tubing 36 between the sensors 102, 104. The flow restrictor can be, for example, a small mechanical orifice, a thin, relatively long tube or conduit, combinations of the same, or the like. By restricting the flow between the two pressure sensors 102, 104, the flow restrictor may better enable the pressure sensors 102, 104 to obtain differential pressure measurements. The pressure differential measurements can be used to calculate the flow rate of air in the tubing 36, as the pressure difference can be proportional to the flow rate. Moreover, in embodiments where thin tubing is used, the length of the tubing can determine the amount of air resistance and hence the amount of pressure difference generated in the tubing. A high flow rate can indicate the presence of a leak in the tubing, wound bed, or the like. If a leak occurs, an alarm can be triggered to alert a clinician. Example circuits for determining air flow, detecting leaks, and/or triggering alarms is shown and described below with respect to FIGS. 13 and 14.

During normal operation, the flow of air through the tubing 36 is sufficiently small such that there may be only a negligible pressure difference between the two pressure sensors 102, 104. However, if there are substantial leaks in the system, the pumps 30a, 30b will run at a higher level of output and air will flow more quickly through the tubing 36, causing the pressure differential between the two sensors 102, 104 to increase to a more easily detectable range. The pressure values collected from the primary pressure sensor 102 and the secondary pressure sensors 102 will preferably provide a pressure differential. In some embodiments, a high flow alarm will be activated when the pressure differential between the two pressure sensors 102, 104 is approximately 5 mmHg or greater. In some embodiments, a high flow alarm will be activated when the pressure differential between the two pressure sensors 102, 104 is approximately 7.5 mmHg or greater. In some embodiments, a high flow alarm will be activated when the pressure differential between the two pressure sensors 102, 104 is approximately 10 mmHg or greater. Additional embodiments using pressure sensors to detect high flow are shown and described below with respect to FIGS. 13 and 14.

Additionally, in some embodiments, the vacuum system control device 32 is preferably configured to comprise an intermittent delay function. In some embodiments, the intermittent delay preferably reduces the overall duty cycle of the pumps 30a, 30b by approximately 20% or more. In some embodiments, the intermittent delay preferably reduces the overall duty cycle of the both pumps 30a, 30b by approximately 30% or more. In some embodiments, the intermittent delay preferably reduces the overall duty cycle of the both pumps 30a, 30b by approximately 40% or more. In some embodiments, the intermittent delay preferably reduces the overall duty cycle of the both pumps 30a, 30b by approximately 50% or more. In this manner, the intermittent delay preferably controls the output of the pumps 30a, 30b so as to cycle the pressure between a range of values. An example intermittent delay circuit is shown and described below with respect to FIG. 14.

Accordingly, the inventors have developed embodiments of a control device and other vacuum pump circuitry that do not include a processor. The control device instead preferably includes analog and/or digital (non-processor) circuitry that increases the efficiency of the control device and, hence, the overall apparatus, as is described in greater detail below. In some implementations, some non-processor digital circuitry can also be provided. Following a discussion of the overall system embodiments set forth in FIGS. 5A-9 below, more detail will be presented regarding some embodiments developed by the inventors to develop a more energy efficient pump controller and NPWT apparatus.

Figure 5A:
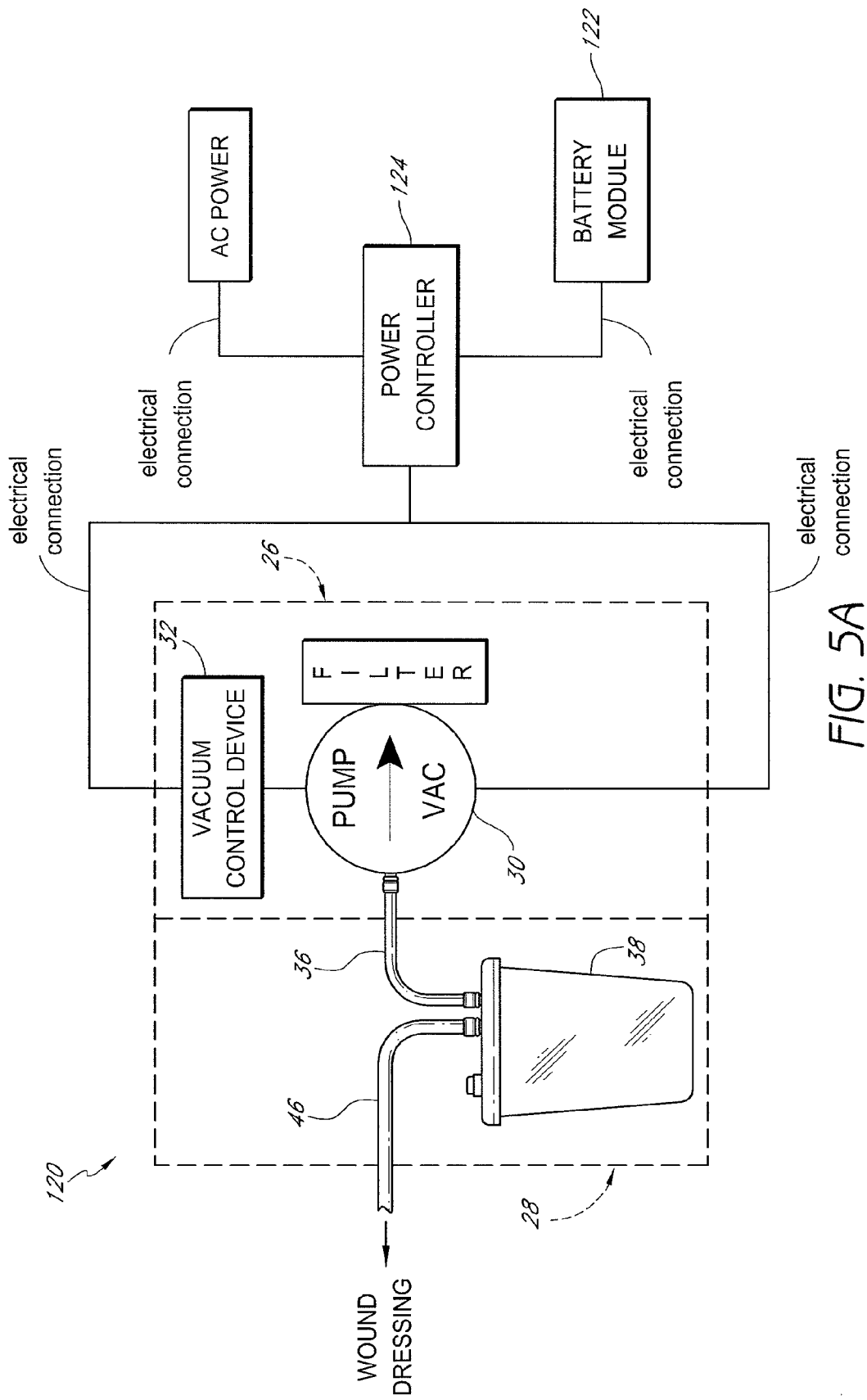
FIG. 5A is a schematic representation of another embodiment of a negative pressure wound therapy apparatus.

FIG. 5A is a schematic illustration of an embodiment of an NPWT apparatus 120 implementing an auxiliary power source—e.g., a battery module 122. As used herein, the phrase auxiliary power source is used to represent any source of power other than an alternating current (AC) power source. As illustrated therein, the NPWT apparatus 120 may receive power from either of two power sources, an AC power supply or a battery module 122. As used throughout this disclosure without regard to context, the term module is used to mean the following terms or any similar terms: element, component, unit, or member. In some embodiments, the battery module 122 may comprise one or more high capacity, rechargeable lithium ion batteries. However, the NPWT apparatus 120 is not limited to the use of a lithium ion battery. The battery module 122 can comprise any suitable rechargeable battery or combination thereof that preferably has high capacity and high efficiency or is suitable for an NPWT apparatus for its designated use. Because it may be beneficial to use the NPWT apparatus 120 in remote areas or where a dependable supply of AC power is not available, the battery module 122 preferably has a high charge capacity and/or high run time. Additionally, as discussed above and more fully below, the vacuum system control device 32 is preferably a high efficiency control device, so as to minimize energy draw from the battery module 122.

As illustrated in FIG. 5A, a power controller 124 preferably interconnects the AC power supply and the battery module 122 to the vacuum system control device 32 and to the vacuum pump 30, depending on the particular electrical needs of each of the devices. As used herein, the term AC power supply can mean any available power source provided to the NPWT apparatus through a wired source. Further, the power controller 124 can be any type of power controller suitable for use with mechanical systems such as NPWT apparatuses.

In some embodiments, the power controller 124 serves at least the following additional functions. First, the power controller 124 preferably provides a supply of electrical current to the battery modules 122 when an AC power supply is connected to the power controller 124. Additionally, in some embodiments, the power controller 124 is preferably configured to serve as a switch between the provision of energy from either the AC power supply or the battery module 122 to the NPWT apparatus 120, depending on whether a sufficient supply of AC power is available for the NPWT apparatus 120. In particular, in some embodiments, the power controller 124 can be configured to provide power from the battery module 122 to the necessary components of the NPWT apparatus 120 when the AC power supply has either been terminated or has attenuated below a predetermined threshold value.

In some embodiments, to account for the scenario where the AC power supply is providing some power, but less than the amount needed by the NPWT apparatus 120, the power controller 124 can be configured to provide an amount of power from the battery module 122 needed to augment the power provided by AC power source. In some embodiments, the power controller may be configured to terminate the provision of power from the battery module 122 to the necessary components of the NPWT apparatus 120 when a sufficient level of power is provided by the AC power supply.

Figure 5B:
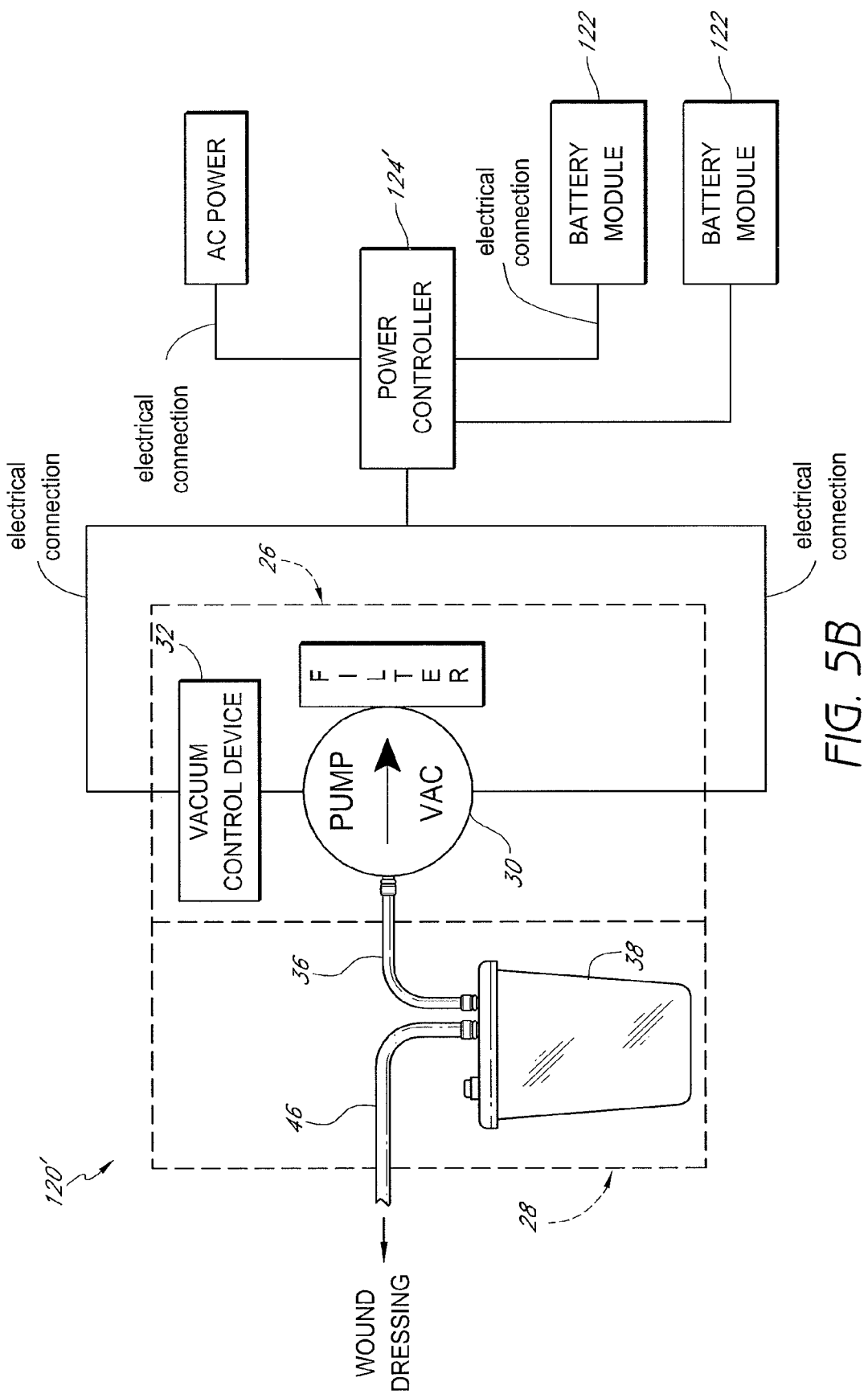
FIG. 5B is a schematic representation of another embodiment of a negative pressure wound therapy apparatus.

In some embodiments, as illustrated in FIG. 5B, the power controller 124' can be configured to control the input of power and the distribution of power among two or more battery modules 122 that are preferably connected to the power controller 124 in parallel. Thus, in the illustrated embodiment, a plurality of battery modules 122 can be interconnected by the power controller 124' and an AC power supply such that a plurality of battery modules 122 provide power to the necessary components of the NPWT apparatus 120'. In some embodiments, the battery modules 122 and power controller 124 may be configured to such that any of the battery modules 122 can be easily disconnected from the power controller 124, 124' and replaced with a different battery module 122, allowing a user to replace a depleted battery module 122 with a charged battery module 122. Finally, because the effectiveness of some types of batteries may diminish more rapidly when they are fully discharged before being recharged, such as lithium ion batteries, some embodiments of the power controller are preferably configured to evenly distribute the energy draw among the battery modules 122 that are connected to the power controller 124 so as to decrease the instance of a full discharge of any single battery.

Figure 6:
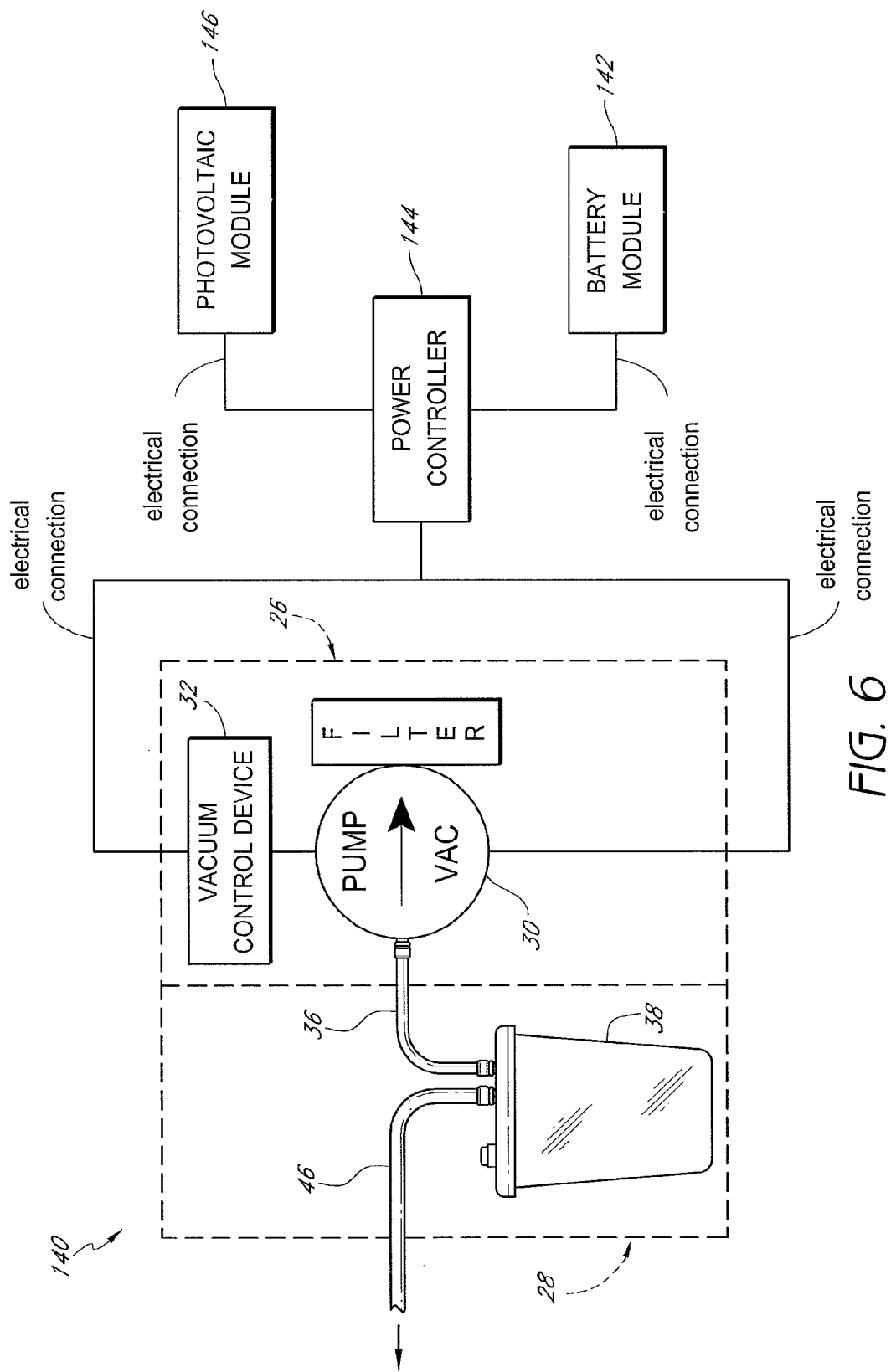
FIG. 6 is a schematic representation of another embodiment of a negative pressure wound therapy apparatus.

FIG. 6 is a schematic illustration of an embodiment of an NPWT apparatus 140 implementing a solar panel or photovoltaic module 146 as an auxiliary power source. In the illustrated embodiment, the NPWT apparatus 140 preferably has a battery module 142 that can be configured to provide the same functionality and benefits as in any of the embodiments described above. Similarly, the power controller 144 can be configured to provide the same functionality and benefits as in any of the embodiments described above. Further, in some embodiments, the NPWT apparatus 140 can have a plurality of battery modules 142 as described above. In some embodiments, the NPWT apparatus 140 does not have any battery modules, but is preferably configured to rely solely on the provision of power from the photovoltaic module 146 to supply the energy needs for the NPWT apparatus 140.

Additionally, the power controller 144 is preferably configured to serve as a switch between the provision of energy from either: just the photovoltaic module 146, or the photovoltaic module 146 and the battery module or modules 142, or just the battery module or modules 142, to the necessary components of the NPWT apparatus 20. In particular, the power controller 144 is preferably configured to provide an electrical current to the necessary components of the NPWT apparatus 20 from the photovoltaic module 146 and the battery module or modules 142, or just the battery module or modules 142, if the energy output from the photovoltaic module 146 alone is not sufficient to meet the energy needs of the NPWT apparatus 20 and if the battery module 142 has an amount of a charge that is greater than zero or greater than a predetermined amount. Accordingly, in some embodiments, the power controller 144 is preferably configured to provide power from the battery module 142 to augment the power provided by the photovoltaic module 146 only when the energy needs of the NPWT apparatus 20 are greater than the supply of energy from the photovoltaic module 146. Further, in some embodiments, the power controller 144 is preferably configured to direct the amount of electricity generated by the photovoltaic module 146 that is above the amount needed by the NPWT apparatus 20 to the optional battery module or modules 142, to recharge the battery module or modules 142 if needed.

Additionally, in some embodiments, the power controller 144 can be configured to also accept an input of energy from an AC power supply. If an AC power supply is present, the power controller 144 will preferably be configured to serve as a control switch between the provision of energy from either the photovoltaic module 146, the battery 142, or the AC power supply to the components of the NPWT apparatus 20. Accordingly, in some embodiments, the power controller 144 can be configured to allow power to be supplied to the necessary components of the NPWT apparatus 140 by all of, or any combination of, the following power sources or any other power sources described herein: an AC power supply, the photovoltaic module 146, or the battery module or modules 142. In some embodiments, when the power supply of either the AC power source or the photovoltaic module 146 is sufficient to meet the energy needs of the NPWT apparatus 140, the power controller is preferably configured to provide power only from the AC power supply and/or photovoltaic module 146, but not from the battery module or modules 142. However, in some embodiments, the power controller 144 can be configured to augment the power provided by the AC power supply or photovoltaic module 146 with the energy available from the battery module or modules 142 to the necessary components of the NPWT apparatus 140 when the power supplied by the AC power supply or photovoltaic module 146 falls below a threshold value and if the battery module 142 has an amount of a energy that is greater than zero or greater than a predetermined amount.

Further, in some embodiments, the power controller 144 is preferably configured to direct the amount of electricity supplied by the photovoltaic module 146 or the AC power supply that is above the amount needed by the respective components of the NPWT apparatus 20 to the optional battery module or modules 142, to recharge the battery module or modules 142 if needed.

The photovoltaic module 146 preferably comprises one or more photovoltaic panels, or otherwise known as solar panels. Each of the solar panels preferably comprises a prepackaged, interconnected collection of individual photovoltaic cells, also referred to as solar cells, which are preferably packaged on a metal or rigid material frame and have a glass covering to keep the photovoltaic cells clean and to protect the photovoltaic cells from impact damage due to dust, debris, or other objects. Further, the individual cells are preferably interconnected by suitable electrically conductive wiring, and may provide a direct current (DC) supply of electricity to the power controller 144. Therefore, in one preferred embodiment, the DC current output from the photovoltaic module 146 may be directly channeled to the power controller 144. The photovoltaic module 146 can be any suitable photovoltaic panel, or can be comprised of any of the commercially available photovoltaic panels now or later developed, such as, but not limited to, those manufactured by General Electric, BP Solar, or Sharp.

In some embodiments, the photovoltaic module 146 may comprise an inverter that is configured to convert the preferably DC output from the photovoltaic cells into an AC current prior to supplying the power to the power controller 144. However, this may be less preferable than in the above-described embodiments because an inverter may decrease the energy efficiency of the NPWT apparatus 140. However, in some embodiments, where the photovoltaic module 146 may be plugged directly into the AC power input in an enclosure used to house the components of the NPWT apparatus 140, it may be preferable to have an inverter convert the power from the photovoltaic module 146 to an AC current prior to supplying such current to the NPWT apparatus 140.

In some embodiments, the photovoltaic module 146 will preferably be capable of producing from approximately one watt to approximately five watts of power, or from approximately five to approximately ten watts of power, or from approximately ten to approximately fifteen watts of power, or from approximately fifteen to approximately twenty watts of power, or from approximately twenty to approximately thirty watts of power, or from approximately thirty to approximately fifty watts of power, or from approximately fifty to approximately seventy watts of power, or from approximately seventy to approximately one hundred watts of power, or from approximately one hundred to approximately one hundred-twenty watts of power, or more than approximately one hundred-twenty watts of power.

Figure 7B:
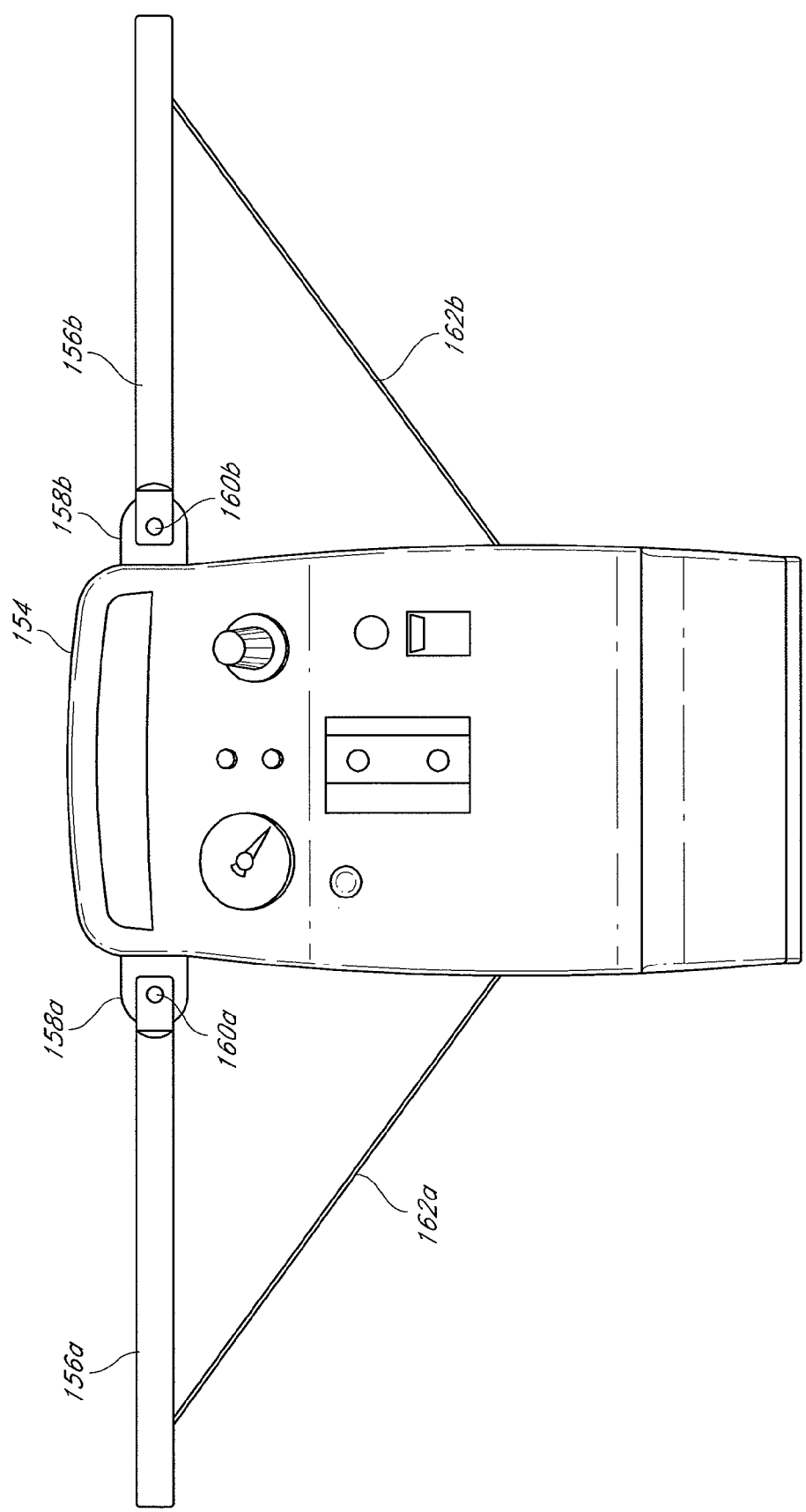
FIG. 7B is a front view of the embodiment of the negative pressure wound therapy apparatus illustrated in FIG. 7A, showing each of the two embodiments of the photovoltaic panel in a substantially extended position.
Figure 7C:
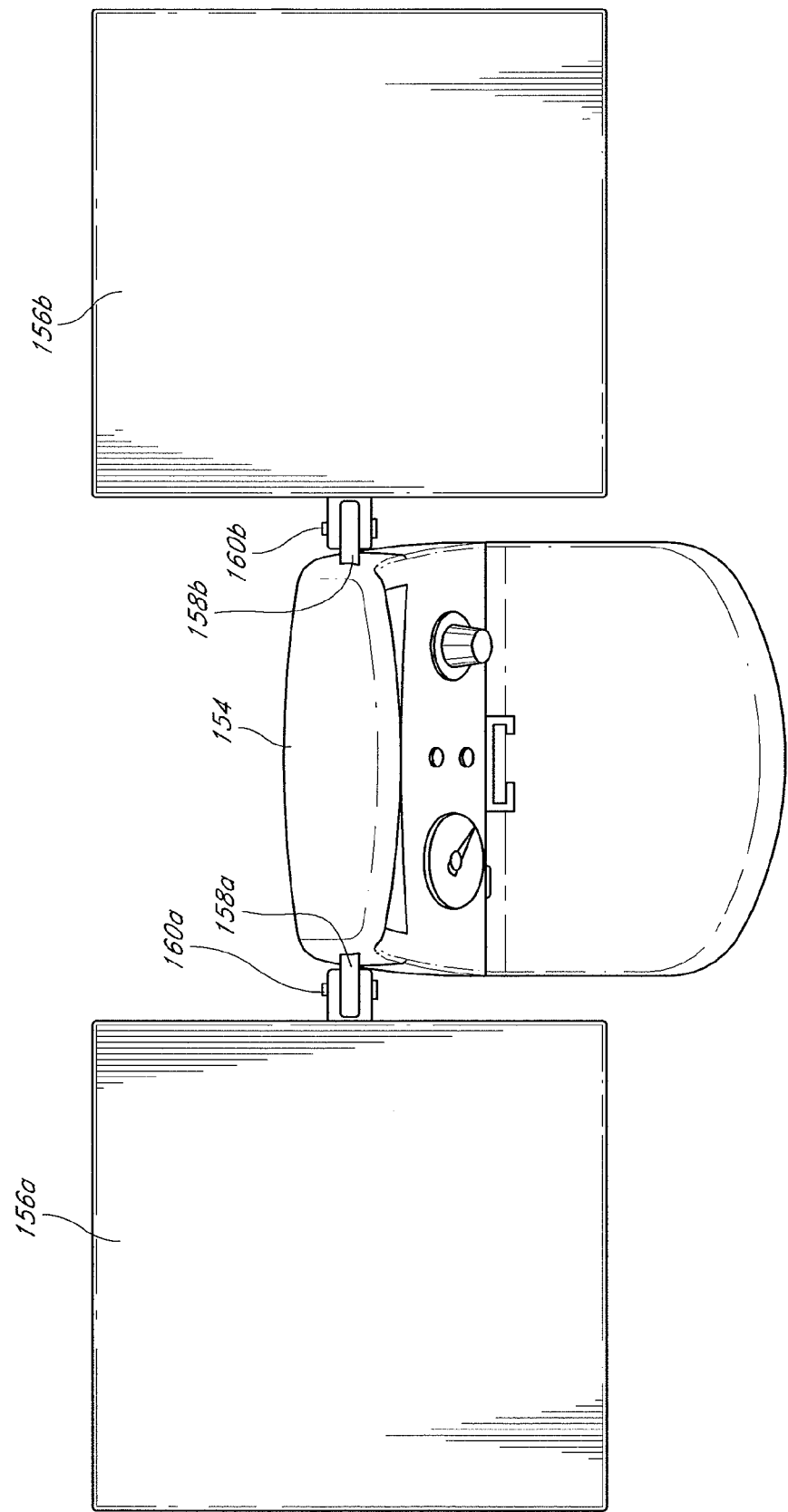
FIG. 7C is a top view of the embodiment of the negative pressure wound therapy apparatus illustrated in FIG. 7A, showing each of the two embodiments of the photovoltaic panel in a substantially extended position.

FIGS. 7A-7B illustrate an embodiment of an NPWT apparatus 150 with the photovoltaic module 152 mounted to an enclosure 154 that is similar to the enclosure 68 described above, but is preferably sized and configured to support the photovoltaic module 152. In the illustrated embodiment, the photovoltaic module 152 preferably comprises two photovoltaic panels 156a and 156b that are preferably mounted to the opposing sides of the enclosure 154. In FIG. 7A, the photovoltaic panels 156a, 156b are each shown in the retracted or stowed position. In this position, the photovoltaic panels 156a, 156b may not be operative, but are in a protected position that allows the easy transport of the NPWT apparatus 150. FIGS. 7B-7C are a front view and a top view, respectively, of the NPWT apparatus 150 showing the photovoltaic panels 156a, 156b in the extended or operative position. As illustrated, in this position, the photovoltaic panels 156a, 156b may gather the necessary solar radiation to provide energy to the necessary components of the NPWT apparatus 150. The NPWT apparatus 150 is preferably configured such that the orientation of each of the photovoltaic panels 156a, 156b can be adjusted so as to optimize solar exposure.

As illustrated in FIGS. 7A-7C, the enclosure 154 can have a pair of flanges 158a, 158b which may extend from the sides of the enclosure 154. The flanges 158a, 158b can provide a mounting support to which a pair of pins or other fasteners 160a, 160b may be fastened to secure or support the photovoltaic panels 156a, 156b to the enclosure 154. In some embodiments, the flanges 158a, 158b and pins 160a, 160b are preferably configured to allow the photovoltaic panels 156a, 156b to rotate freely about a centerline axis defined through each of the two pins 160a, 160b. A pair of support arms 162a, 162b may be used to support each of the photovoltaic panels 156a, 156b in their desired position relative to the enclosure 154. In some embodiments, the support arms 162a, 162b are configured to be secured to each of the photovoltaic panels 156a, 156b such that they are free to rotate relative to the photovoltaic panels 156a, 156b, enabling a user of the NPWT apparatus 150 to position the support arms 162a, 162b at any desired angular orientation. Each side of the enclosure 154 as well as the ends of each of the support arms 162a, 162b may be configured so as to provide features that secure the ends of the support arms 162a, 162b at the desired position. Such features may include, but are not limited to, pins, protrusions, holes, depressions, teethed protrusions, channels, or velcro.

In some embodiments, to increase the adjustability of the orientation of the photovoltaic panels 156a, 156b, the photovoltaic panels 156a, 156b may be fastened to the enclosure 154 using one or more friction damped universal joints or any other suitable joint components that may securely fasten the photovoltaic panels 156a, 156b to the enclosure 154 and allow increased adjustability. The friction damped universal joints would preferably be configured to allow the one or more photovoltaic panels 156a, 156b supported by the enclosure 154 to have multiple degrees of freedom. In some embodiments, each of the one or more photovoltaic panels 156a, 156b would preferably be adjustable so as to rotate about two axes—i.e., to tilt up and down from a stowed to any of a wide range of operative angular orientations, as well as to rotate or twist about the joint to increase the solar exposure of each of the photovoltaic panels 156a, 156b. In some embodiments, the NPWT apparatus 150 can be configured such that the orientation of the photovoltaic panels 156a, 156b is automated, so as to orient the photovoltaic panels 156a, 156b in the most effective orientation based on the location of the sun.

In some embodiments, the photovoltaic module 146 can be integrated into the enclosure 154 of the NPWT apparatus 140 (as illustrated in FIG. 7) or can be any of the commercially available stand alone or free standing modules and can be connected to the NPWT apparatus 140 by a sufficiently long electrically conductive wire that may permit the photovoltaic module 146 to be positioned at a long distance away from the other components of the NPWT apparatus 140. In particular, the user of the NPWT apparatus 140 may desire to position the photovoltaic module 146 in an outdoor location for maximum solar exposure, while the patient and the remaining components of the NPWT apparatus 140 are preferably positioned indoors or under cover of a tent or other structure. A commercially available stand alone photovoltaic module 146 can be used as the auxiliary power source in this situation.

Figure 8:
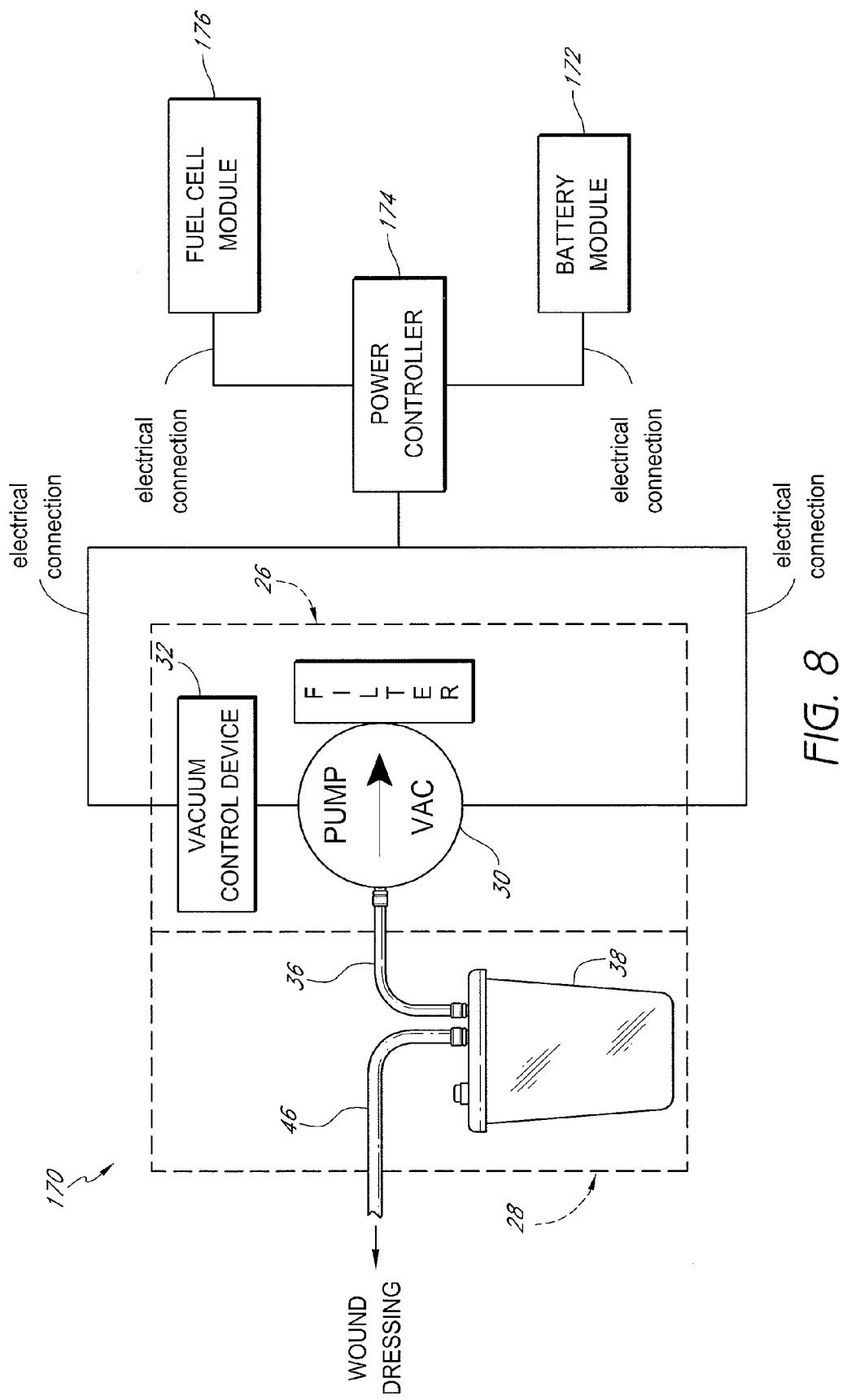
FIG. 8 is a schematic representation of another embodiment of a negative pressure wound therapy apparatus.

FIG. 8 is a schematic illustration of an embodiment of an NPWT apparatus 170 implementing a fuel cell module 176 as an auxiliary power source. In the illustrated embodiment, the NPWT apparatus 170 preferably has a battery module 172 that can be configured to provide the same functionality and benefits as in any of the embodiments described above. Similarly, the power controller 174 can be configured to provide the same functionality and benefits as in any of the embodiments described above. In some embodiments, the NPWT apparatus 170 can have a plurality of battery modules 172 as described above. In some embodiments, the NPWT apparatus 170 does not have any battery modules, but is configured to rely solely on the provision of power from the fuel cell module 176 to supply the energy needs for the NPWT apparatus 170.

Additionally, the power controller 174 is preferably configured to serve as a switch between the provision of energy from either: just the fuel cell module 176, or the fuel cell module 176 and the battery module or modules 172, or just the battery module or modules 172 to the necessary components of the NPWT apparatus 20. In particular, the power controller 174 is preferably configured to provide an electrical current to the necessary components of the NPWT apparatus 20 from the fuel cell module 176 and the battery module or modules 172, or just the battery module or modules 172, if the energy output from the fuel cell module 176 alone is not sufficient to meet the energy needs of the NPWT apparatus 20 and if the battery module 172 has an amount of a charge that is greater than zero or greater than a predetermined amount. Accordingly, in some embodiments, the power controller 174 is preferably configured to provide power from the battery module 172 to augment the power provided by the fuel cell module 176 only when the energy needs of the NPWT apparatus 20 are greater than the supply of energy from the fuel cell module 176. Further, in some embodiments, the power controller 174 is preferably configured to direct the amount of electricity generated by the fuel cell module 176 that is above the amount needed by the NPWT apparatus 20 to the optional battery module or modules 172, to recharge the battery module or modules 172 if needed.

Additionally, in some embodiments, the power controller 174 can be configured to also accept an input of energy from an AC power supply. If an AC power supply is present, the power controller 174 will preferably be configured to serve as a control switch between the provision of energy from either the fuel cell module 176, the battery 172, or the AC power supply to the components of the NPWT apparatus 20. Accordingly, in some embodiments, the power controller 174 can be configured to allow power to be supplied to the necessary components of the NPWT apparatus 170 by all of, or any combination of, the following power sources or any other power sources described herein: an AC power supply, the fuel cell module 176, or the battery module or modules 172. In some embodiments, the power controller is preferably configured to provide power only from the AC power supply and/or fuel cell module 176, but not from the battery module or modules 172, when the power supply of either the AC power source or the fuel cell module 176 is sufficient to meet the energy needs of the NPWT apparatus 20. However, in some embodiments, the power controller 174 can be configured to augment the power provided by the AC power supply or fuel cell module 176 with the energy available from the battery module or modules 172 to the necessary components of the NPWT apparatus 170 when the power supplied by the AC power supply or fuel cell module 176 falls below a threshold value and if the battery module 172 has an amount of a energy that is greater than zero or greater than a predetermined amount.

Further, in some embodiments, the power controller 174 is preferably configured to direct the amount of electricity supplied by the fuel cell module 176 or the AC power supply that is above the amount needed by the respective components of the NPWT apparatus 20 to the optional battery module or modules 172, to recharge the battery module or modules 172 if desired.

In some embodiments, the fuel cell module 176 can be integrated into the casing or enclosure housing the NPWT apparatus 170, such as, but not limited to, the commercially available H-30 PEM Fuel Cell System, available from the Fuel Cell Store located in Boulder, Colo., United States of America. In some embodiments, the fuel cell module 176 can be a free standing or a portable fuel cell system of the type that is commercially available, such as, but not limited to, the Automatic Battery Charger manufactured by the Voller Energy Group, PLC (located in Basingstoke, Hampshire, United Kingdom), the EFOY 600 methanol fuel cell, or the EFOY 1600 methanol fuel cell, all available from the Fuel Cell Store located in Boulder, Colo., United States of America.

In some embodiments, the fuel cell module 176 will preferably be capable of producing from approximately one watt to approximately five watts of power, or from approximately five to approximately ten watts of power, or from approximately ten to approximately fifteen watts of power, or from approximately fifteen to approximately twenty watts of power, or from approximately twenty to approximately thirty watts of power, or from approximately thirty to approximately fifty watts of power, or from approximately fifty to approximately seventy watts of power, or from approximately seventy to approximately one hundred watts of power, or from approximately one hundred to approximately one hundred-twenty watts of power, or more than approximately one hundred-twenty watts of power.

Figure 9:
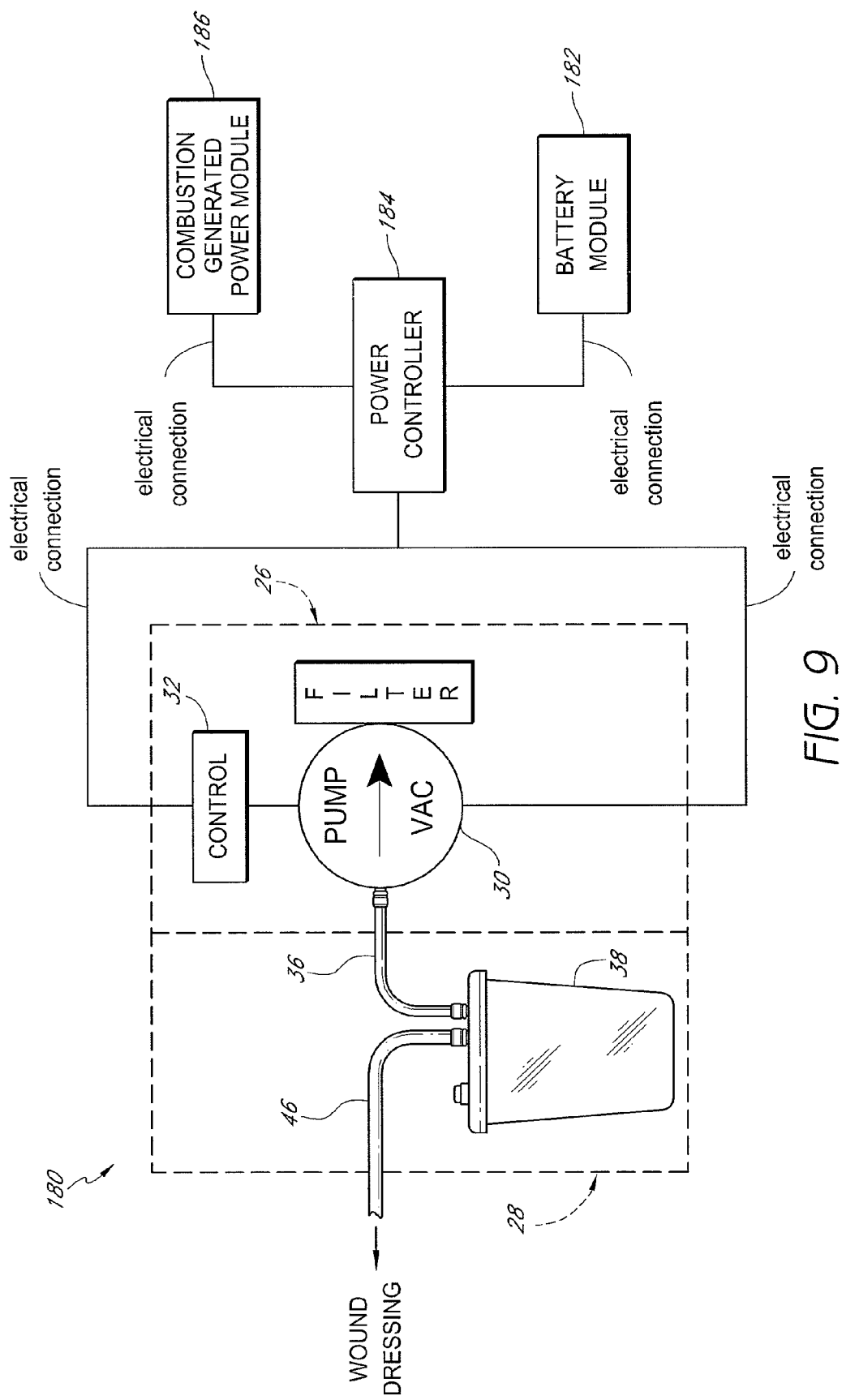
FIG. 9 is a schematic representation of another embodiment of a negative pressure wound therapy apparatus.

FIG. 9 is a schematic illustration of an embodiment of an NPWT apparatus 180 implementing a combustion generated power module 186 as an auxiliary power source. In the illustrated embodiment, the NPWT apparatus 180 preferably has a battery module 182 that can be configured to provide the same functionality and benefits as in any of the embodiments described above. Similarly, the power controller 184 can be configured to provide the same functionality and benefits as in any of the embodiments described above. In some embodiments, the NPWT apparatus 180 can have a plurality of battery modules 182 as described above. In some embodiments, the NPWT apparatus 180 does not have any battery modules, but is configured to rely solely on the provision of power from the combustion generated power module 186 to supply the energy needs for the NPWT apparatus 180.

Additionally, the power controller 184 is preferably configured to serve as a switch between the provision of energy from either: just the combustion generated power module 186, or the combustion generated power module 186 and the battery module or modules 182, or just the battery module or modules 182 to the necessary components of the NPWT apparatus 20. In particular, the power controller 184 is preferably configured to provide an electrical current to the necessary components of the NPWT apparatus 20 from the combustion generated power module 186 and the battery module or modules 182, or just the battery module or modules 182, if the energy output from the combustion generated power module 186 alone is not sufficient to meet the energy needs of the NPWT apparatus 20 and if the battery module 182 has an amount of a charge that is greater than zero or greater than a predetermined amount. Accordingly, in some embodiments, the power controller 184 is preferably configured to provide power from the battery module 182 to augment the power provided by the combustion generated power module 186 only when the energy needs of the NPWT apparatus 20 are greater than the supply of energy from the combustion generated power module 186. Further, in some embodiments, the power controller 184 is preferably configured to direct the amount of electricity generated by the combustion generated power module 186 that is above the amount needed by the NPWT apparatus 20 to the optional battery module or modules 182, to recharge the battery module or modules 182 if needed.

Additionally, in some embodiments, the power controller 184 can be configured to also accept an input of energy from an AC power supply. If an AC power supply is present, the power controller 184 will preferably be configured to serve as a control switch between the provision of energy from either the combustion generated power module 186, the battery 182, or the AC power supply to the components of the NPWT apparatus 20. Accordingly, in some embodiments, the power controller 184 can be configured to allow power to be supplied to the necessary components of the NPWT apparatus 180 by all of, or any combination of, the following power sources or any other power sources described herein: an AC power supply, the combustion generated power module 186, or the battery module or modules 182. In some embodiments, the power controller is preferably configured to provide power only from the AC power supply and/or combustion generated power module 186, but not from the battery module or modules 182, when the power supply of either the AC power source or the combustion generated power module 186 is sufficient to meet the energy needs of the NPWT apparatus 20. However, in some embodiments, the power controller 184 can be configured to augment the power provided by the AC power supply or combustion generated power module 186 with the energy available from the battery module or modules 182 to the necessary components of the NPWT apparatus 180 when the power supplied by the AC power supply or combustion generated power module 186 falls below a threshold value and if the battery module 182 has an amount of a energy that is greater than zero or greater than a predetermined amount.

Further, in some embodiments, the power controller 184 is preferably configured to direct the amount of electricity supplied by the combustion generated power module 186 or the AC power supply that is above the amount needed by the respective components of the NPWT apparatus 20 to the optional battery module or modules 182, to recharge the battery module or modules 182 if desired.

In some embodiments, the combustion generated power module 186 can be integrated into the casing or enclosure housing the NPWT apparatus 180 or can be any of the commercially available free standing portable generator systems such as, but not limited to, the EU 1000i manufactured by the American Honda Power Equipment Division, or the Briggs & Stratton Portable Generator BS-1532. Further, because power generators are available in a wide ranging variety of power outputs, multiple NPWT apparatuses could be powered by a single combustion generated power module.

In some embodiments, the combustion generated power module 186 will preferably be capable of producing from approximately one watt to approximately ten watts of power, or from approximately ten to approximately twenty watts of power, or from approximately twenty to approximately forty watts of power, or from approximately forty to approximately eighty watts of power, or from approximately eighty to approximately one hundred twenty watts of power, or from approximately one hundred twenty to approximately one hundred sixty watts of power, or more than approximately one hundred sixty watts of power.

In some embodiments, the combustion generated power module 186 can be integrated into the NPWT apparatus 180, or can be any of the commercially available stand alone or free standing modules and can be connected to the NPWT apparatus 180 by a sufficiently long electrically conductive wire that may permit the combustion generated power module 186 to be positioned at a long distance away from the other components of the NPWT apparatus 180. In particular, the user of the NPWT apparatus 180 may desire to position the combustion generated power module 186 in an outdoor or ventilated location to minimize the patient's and user's exposure to the noise and/or exhaust resulting from the operation of the combustion generated power module 186.

Additionally, in some embodiments, a human powered generator can be used in place of the combustion generated power module 186 discussed above to supply the necessary amount of energy to any of the NPWT apparatuses described herein. The human powered generator can be any of the commercially available portable generator systems such as, but not limited to, the Pedal-A-Watt stationary bike power generator, any of the wide range of hand operated dynamos that are available, or any other human powered generators that are currently available or later developed.

While the foregoing auxiliary power systems were described in connection with certain embodiments of NPWT apparatuses, the present disclosure is not so limited. The foregoing auxiliary power systems described herein can be used, or configured to be used, without undue experimentation, with any NPWT apparatus that is desired or that is known in the art. For example, without limitation, any of the foregoing auxiliary power systems can be used, or configured to be used without undue experimentation, with the NPWT system described in U.S. Patent Application Publication No. US 2004/0073151 A1, which disclosure is incorporated by reference herein and made a part of the present specification.

Figure 10:
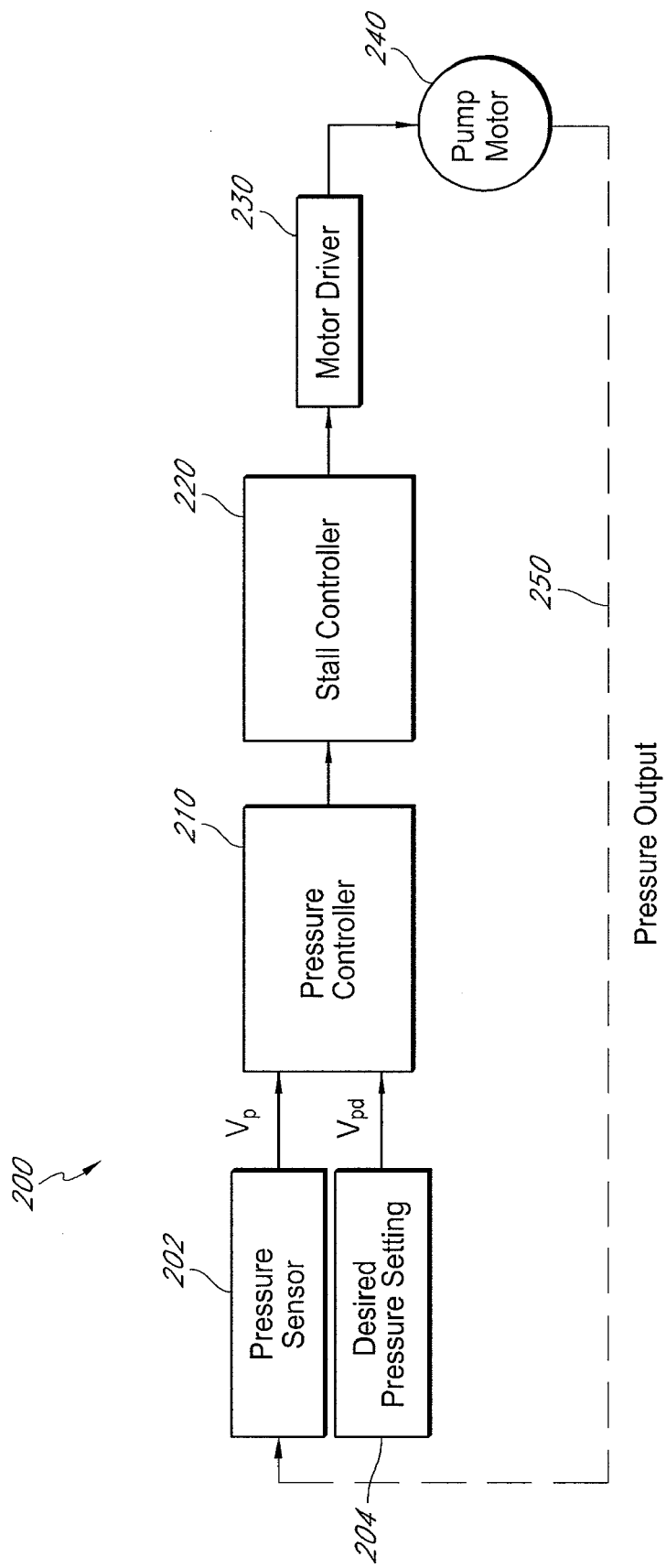
FIG. 10 is a block diagram of an embodiment of a pressure control circuit.

FIG. 10 illustrates an embodiment of a pressure control circuit 200. The pressure control circuit 200 controls the pressure in the plumbing of one or more vacuum pumps, such as any of the vacuum pumps described above. Certain embodiments of the pressure control circuit 200 advantageously control the pressure of the pump plumbing without using a microcontroller.

In the pressure control circuit 200, a pressure sensor 202 or the like is provided as a transducer for converting sensed pressure in the pump plumbing into a pressure voltage $V_p$. The pressure sensor 202 can include, for example, a piezoelectric material that alters its electrical characteristics as pressure at the piezoelectric material changes. The pressure of the pump system, and hence the pressure voltage $V_p$, can change over time. Thus, the pressure voltage $V_p$ can be a time-varying voltage signal.

A desired pressure voltage $V_{pd}$ is also provided to the pressure controller 210 by a desired pressure setting 204. The desired pressure setting 204 can be a hardwired pressure setting (e.g., using a resistor network or the like) or a user-defined pressure setting. The desired pressure setting 204 can be provided, for example, by an input device such as a knob or button that can be adjusted by a user. In one embodiment, described below, the desired pressure setting 204 is provided using an encoder that converts a value on a knob or dial into the desired pressure voltage $V_{pd}$.

The pressure voltage $V_p$ and desired pressure voltage $V_{pd}$ can be provided to a pressure controller 210. In certain embodiments, the pressure controller 210 includes one or more circuit components for adjusting the pressure provided by a pump motor 240 such that the pressure voltage is the same or substantially the same as the desired pressure voltage. Advantageously, the pressure controller 210 of certain embodiments includes analog circuit components rather than a processor such as a microcontroller. In some implementations, some non-processor digital circuitry can also be provided.

The pressure controller 210 uses the pressure voltage $V_p$ and the desired pressure voltage signal $V_{pd}$ to control the pressure in the pump plumbing. The pressure controller 210 can control the pressure by causing or by attempting to cause the pressure sensed by the pressure sensor 202 to be equal to or substantially equal to the desired pressure setting 204. The pressure controller 210 therefore attempts to keep the pressure voltage $V_p$ close to the desired pressure voltage $V_{pd}$.

The pressure controller 210 of certain embodiments changes pressure in the pump plumbing by adjusting the power, voltage, or current provided to the pump motor 240. By adjusting one or more of these parameters (e.g., power), the pressure controller 210 can increase or decrease the speed of the pump motor 240. As the pump motor 240 increases or decreases speed, the pressure output 250 generated by the pump motor 240 increases or decreases respectively. Thus, by controlling the power or the like sent to the pump motor 240, the pressure controller 210 can control the pressure in the pump plumbing.

As an example, if the pressure voltage $V_p$ is less than the desired pressure voltage $V_{pd}$, the pressure controller 210 can increase the speed of the pump motor 240. As the pump motor increases speed 240, the pressure sensed by the pressure sensor 202 increases, and hence the pressure voltage $V_p$ increases. If, on the other hand, the pressure voltage $V_p$ is less than the desired pressure voltage $V_{pd}$, the pressure controller 210 can decrease the speed of the pump motor 240, thereby causing pressure to fall and the pressure voltage $V_p$ to decrease. In certain embodiments, the pressure controller 210 continually increases and decreases the speed of the pump motor 240 to compensate for decreases and increases in pressure voltage $V_p$, respectively. However, certain override circuits, such as an intermittent delay circuit described below with respect to FIG. 14, can halt the continuous adjustments made by the pressure controller 210.

The pressure controller 210 could be used as the sole pump motor 240 controller in some implementations. However, the pump motor 240 can stall when not enough power is provided to the pump motor 240 to make the coils of the pump motor 240 turn. In stall conditions, the power provided to the pump motor 240 can be wasted. Stalling can occur, for example, when the pressure voltage $V_p$ is higher than the desired pressure voltage $V_{pd}$. To compensate for the higher pressure voltage $V_p$, the pressure controller 210 might reduce the power provided to the pump motor 240. If the pressure controller 210 causes too little power to be provided, the pump motor 240 will stall.

To prevent stalling from occurring, a stall controller 220 is provided that receives one or more output signals from the pressure controller 210. The stall controller 220 of certain embodiments cuts power to the pump motor 240 in the event of an impending stall condition. The stall controller 220 can do this by, for example, overriding the pressure controller 210. Advantageously, the stall controller 220 can prevent stall conditions without using a processor. Instead, the stall controller 220 of various embodiments includes analog and/or digital (non-processor) circuitry that efficiently prevents the pump motor 240 from stalling.

For example, the stall controller 220 can include logic such as an AND gate or the like. The stall controller 220 can generate an override signal that is gated at the AND gate with an output signal from the pressure controller 210. In an embodiment, the override signal is active-low. Thus, if the override signal is at a high voltage or logic state, the override signal enables the output from the pressure controller 210 to effectively pass through the AND gate. If, however, the override signal is at a low voltage or logic state, the override signal can override the output from the pressure controller 210, effectively preventing this output from reaching the pump motor 240. It should be understood that while the override signal has been described as an active-low signal, the override signal can also be active-high in some implementations. Likewise, other active-low signals described herein can be active-high in some embodiments, and vice versa.

In certain embodiments, the output of the stall controller 220 is a combined control signal, which is provided to a motor driver 230. The motor driver 230 facilitates providing power to the pump motor 240. In an embodiment, the motor driver 230 includes one or more transistors (e.g., MOSFETs), relays, or the like that act as a power switch responsive to the combined control signal. A more detailed example of a motor driver 230 is shown and described below with respect to FIG. 14.

Figure 11:
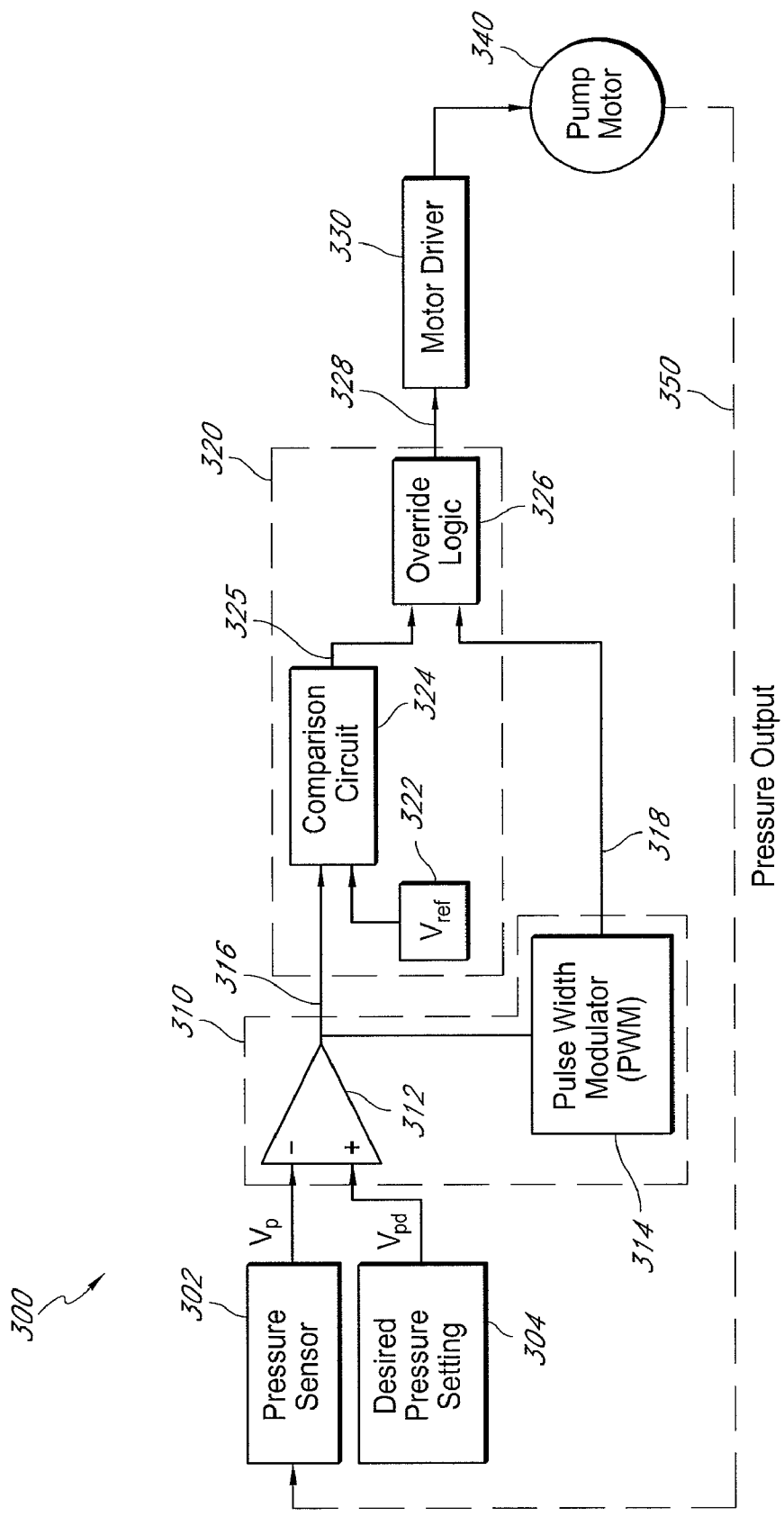
FIG. 11 is a schematic block diagram of another embodiment of a pressure control circuit.

FIG. 11 illustrates a more detailed embodiment of a pressure control circuit 300. The depicted embodiment of the pressure control circuit 300 includes several of the components of the pressure control circuit 200. For example, a pressure sensor 302, a desired pressure setting 304, a motor driver 330, and a pump motor 340 are provided. In certain embodiments, these components have the same functions as those described above with respect to FIG. 10. In addition, more detailed views of a pressure control circuit 310 and a stall control circuit 320 are provided.

The pressure control circuit 310 of certain embodiments includes a difference circuit 312 in communication with a pulse width modulator 314. In one embodiment, the difference circuit 312 includes an amplifier, such as a differential amplifier. The difference circuit 312 receives a pressure voltage $V_p$ from the pressure sensor 302 and a desired pressure voltage $V_{pd}$ from the desired pressure setting 304. The difference circuit 312 can determine a difference in voltage between the pressure voltage $V_p$ and the desired pressure voltage $V_{pd}$ to output a difference signal 316. this difference signal 316 can also be referred to as an error signal because the difference signal 316 can represent the error between the desired pressure voltage $V_{pd}$ and the actual pressure voltage $V_p$. In addition, the difference circuit 312 can amplify the difference between the two voltages. The amplification value can be unity in certain implementations.

In various embodiments, the difference circuit 312 includes an operational amplifier or "op amp." A network of passive circuit elements, such as resistors, capacitors, and/or the like, can be provided on the inputs, outputs, and in a feedback loop of the difference circuit 312. These passive circuit elements can be used to adjust the amplification value or gain of the amplifier and/or the frequency characteristics of the amplifier. A more detailed embodiment of the difference circuit 312 having a network of passive circuit elements is described below with respect to FIG. 14.

In one embodiment, the difference circuit 312 has a gain value of about 6; however, this gain value can take on many other values in other embodiments. In addition, the difference signal 316 in some embodiments is not a pure difference between the pressure voltage $V_p$ and the desired pressure voltage $V_{pd}$. Instead, the difference circuit 312 can be configured with supporting passive circuits elements such that the difference signal 316 is represented as:

$$A*(V_p-V_{pd})+V_{pd}, \quad (1)$$

where A in expression (1) is an amplification or gain value.

The difference signal 316 is provided to the pulse width modulator 314 and to the stall controller 320. The pulse width modulator 314 of certain embodiments includes a comparator, op amp, or the like having supporting passive circuit components for generating a variable duty cycle square wave. This square wave is provided by the pulse width modulator 314 as a motor control signal 318 to the stall controller 320. A more detailed example of a comparator circuit for implementing the pulse width modulator 314 is shown and described below with respect to FIG. 14.

The square wave of the motor control signal 318 is selectively provided, through the stall controller 320, to the motor driver 330. When the motor control signal 318 is in a logic high state, the motor control signal 318 causes the motor driver 330 to provide power to the pump motor 340. Conversely, when the motor control signal 318 is in a logic low state, the motor control signal 318 prevents the motor driver 330 from providing power to the pump motor 340. The motor control signal 318 can accomplish this by actuating a transistor (e.g., MOSFET) or relay power switch. Thus, as the duty cycle of the motor control signal 318 increases, power is provided more frequently to the pump motor 340, causing the speed of the pump motor 340 to increase, and vice versa. Advantageously, using pulse width modulation enables speed control of the pump motor 340 without loss of torque.

The square wave of the motor control signal 318 can have a duty cycle ranging from 0% to 100%. The duty cycle is controlled in certain embodiments by the difference signal 316. As the difference signal 316 increases, the duty cycle can increase, and vice versa. Thus, as the difference (or error) signal 316 increases in magnitude, the duty cycle can increase, and as the difference signal 316 decreases, the duty cycle can decrease. In an embodiment, the pressure controller 310 therefore acts as a proportional controller, changing the speed of the motor in proportion to the amount of error. In other embodiments, integral and/or derivative control can be provided in addition to proportional control, such as to create a proportional-integral-derivative (PID) controller.

Both the difference signal 316 and the motor control signal 318 can be provided to the stall controller 320. In certain implementations, the stall controller 320 includes a comparison circuit 324 and override logic 326. In addition, the stall controller 320 can include or receive a voltage reference 322. The stall controller 320 advantageously prevents the pump motor 340 from stalling, thereby increasing the efficiency of the pressure control system 300.

The comparison circuit 324 includes a comparator, an op amp in comparator configuration, or the like. The comparison circuit 324 compares the difference signal 316 to the voltage reference 322 to produce an override signal 325. In one embodiment, if the difference signal 316 is greater than the voltage reference 322, the comparison circuit 324 outputs a logic high (or high voltage) value. On the other hand, if the difference signal 316 is less than the voltage reference 322, the comparison circuit 324 outputs a logic low (or low voltage) value. Thus, the override signal 325 is high or low depending on whether the difference signal 316 is higher or lower than the voltage reference 322, which is a predetermined threshold voltage value. In certain embodiments, the override signal 325 can be considered active low, meaning that the override signal 325 overrides the motor control signal 318 when the override signal 325 is low.

Accordingly, if the difference (error) signal 316 is greater than the voltage reference 322, the comparison circuit 324 effectively determines that the error is sufficiently high to allow the pressure controller 310 to control the pump motor 340. However, if the difference (error) signal 316 is lower than the voltage reference 322, then the comparison circuit 324 effectively determines that the error is too low, such that the pressure controller 310 might stall the pump motor 340. In this low error situation, the comparison circuit 324 can use the override signal 325 to override the pressure control circuit 310, thereby preventing stalling of the pump motor 340.

While the pump motor 340 is off, the pressure in the pump tubing will drop. As a result, the error or difference signal 316 will increase. Eventually, the difference signal 316 will increase enough to cause the comparison circuit 324 to deactivate the override signal 325, so that the stall controller 320 will allow the pressure controller 310 to take over control of the pump motors 340 again.

While a single voltage reference 322 is shown, an additional voltage reference is provided to enable the comparison circuit 324 to provide hysteresis. In an embodiment, the two voltage references are offset from one another by an optionally small voltage amount. For example, depending on the type, manufacturer, and/or part number of the pressure sensor 302 or other components used, one voltage reference could be set at 1.0 volts and the other voltage reference could be set at 1.2 volts. Other voltage values could be chosen in various embodiments, as is described in more detail below with respect to FIG. 9. If the difference signal 316 is above the higher voltage reference, the comparison circuit 324 outputs a logic high value. If the difference signal 316 is below the lower voltage reference, the comparison circuit 324 outputs a logic low value. If the difference signal 316 is between the two voltage references, the comparison circuit 324 does not change the override signal 325 value. Hysteresis can prevent the comparison circuit 324 from switching rapidly in response to minor changes in the difference signal 316.

The override signal 325 is provided, in certain embodiments, to the override logic 326. The override logic 326 includes one or more analog or digital circuit components that facilitating selectively overriding the motor control signal

318. For instance, the override logic 326 can include an AND gate or the like. As described above, the override signal 325 can be gated at the AND gate with the motor control signal 318, facilitating the selective overriding of the motor control signal 318. The override logic 326 outputs a combined control signal 328 that is provided to the motor driver 330. The combined control signal 328 can reflect the combined control of the pressure controller 310 and the stall controller 320. Thus, if the override signal 325 is high (or not active) in one embodiment, then the combined control signal 328 is effectively the motor control signal 318. However, if the override signal 325 is low (or active), then the combined control signal 328 has a low (not active) output, which does not drive the motor driver 330 and therefore prevents the pump motor 340 from stalling.

While the override circuit 324 has been described with respect to an AND gate, other circuit components can be used. For example, one or more OR, NAND, NOR, XOR, combinations of the same, or other gates can be configured to provide an AND function. In addition, discrete or integrated transistor components can be used to accomplish an AND function. Moreover, in other embodiments, analog circuit components can be used to accomplish an equivalent AND function. Other logic functions, such as the OR, NAND, NOR, XOR, or other functions, could also be used in place of the AND function.

In certain implementations, the stall controller 320 uses the override signal 325 to effectively keep the duty cycle of the pulse width modulator 314 within a certain range during a steady state of the pump motor 340. An ideal duty cycle in one embodiment is 40%. In another embodiment, a desired duty cycle range is 40% to 45%. In still other embodiments, the desired range is 35% to 45%.

Viewed another way, in certain embodiments the pressure control circuit 310 provides linear control and the stall control circuit 320 provides nonlinear control. If the duty cycle of the pulse width modulator 314 is above a target duty cycle value, e.g., 40%, the pressure control system 300 may be operating in linear control mode, using the pressure control circuit 310. If the duty cycle falls below this range, however, the pressure control system 300 may operate in nonlinear mode, using the stall controller 320.

Figure 12A:
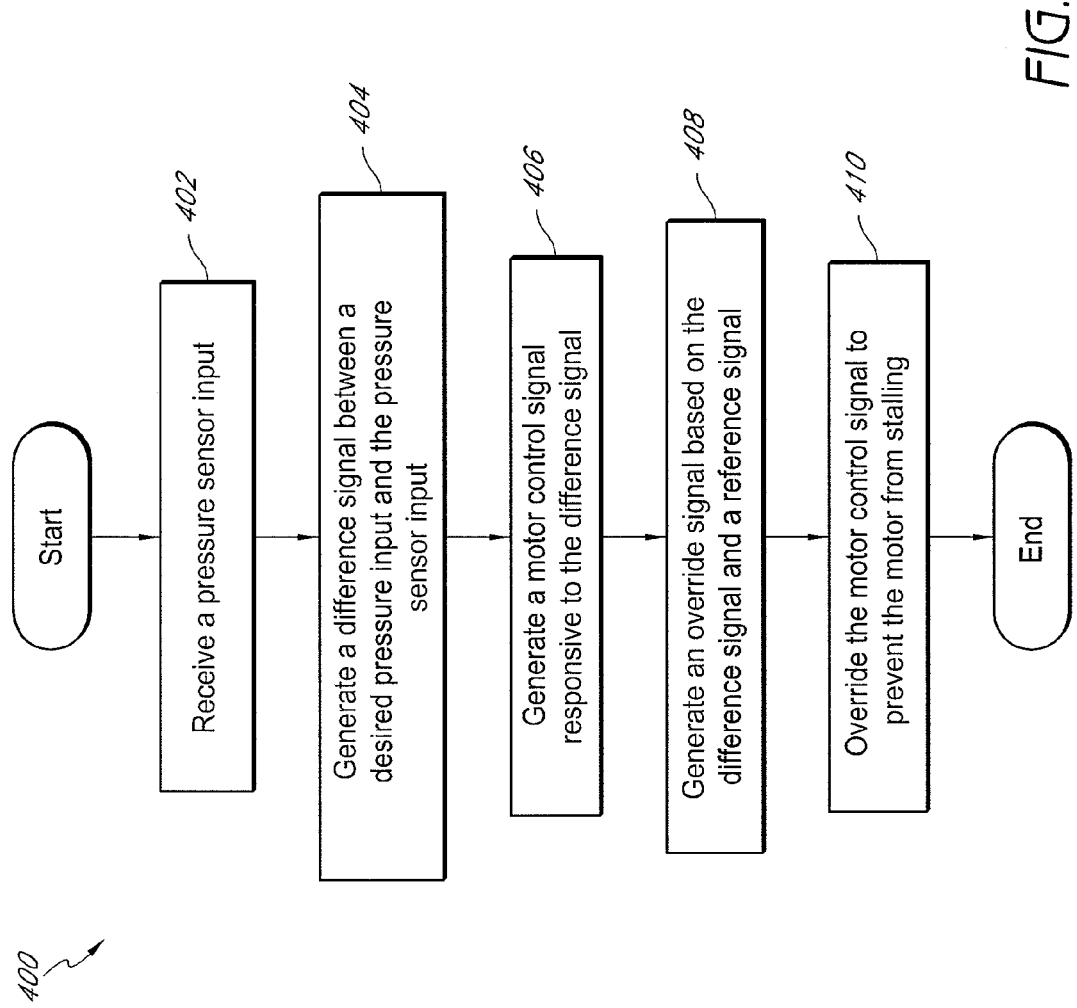
FIG. 12A is an embodiment of a process for controlling a pump motor.

FIG. 12A illustrates an embodiment of a process 400 for controlling a pump motor. The process 400 can be implemented in certain embodiments by any of the pressure control systems described above. Advantageously, the process 400 can therefore be implemented without using a processor. Moreover, the process 400 can be used in conjunction with negative wound pressure therapy techniques, such as those described above.

The process 400 begins at block 402 by receiving a pressure sensor input. The pressure sensor input can be a voltage or current signal from a pressure sensor. In an embodiment, this input is provided by a pressure sensor, such as any of the pressure sensors described above. At block 404, the process 400 generates a difference signal between a desired pressure input and the pressure sensor input. The desired pressure input can be provided by, for example, a user through an input device. The difference signal can represent an error between desired and actual pressure inputs. This difference signal can be used to control the speed of a pump motor.

Continuing, at block 406 the process 400 generates a motor control signal responsive to the difference signal. The motor control signal can be a pulse-width modulated signal or have other signal characteristics. At block 408, the process 400 generates an override signal based at least in part on the difference signal and on at least one reference signal. One or more reference signals can be provided to compare with the difference signal. If the difference signal is above or below a reference signal, for instance, the process 400 can perform certain actions. For example, at block 410, the process 400 can override the motor control signal to prevent the motor from stalling.

In certain embodiments, the process 400 overrides the motor control signal in response to the difference signal being lower than at least one reference signal. As the pressure increase due to the turning off of the pump motor, the difference signal will increase until the difference signal is above the reference signal. At this point, the override signal will deactivate, allowing the motor control signal to control the speed of the pump motor.

Advantageously, the process 400 provides for motor control without stalling a motor. In particular, the process 400 increases the efficiency of power usage by the motor by avoiding stalling conditions.

Figure 12B:
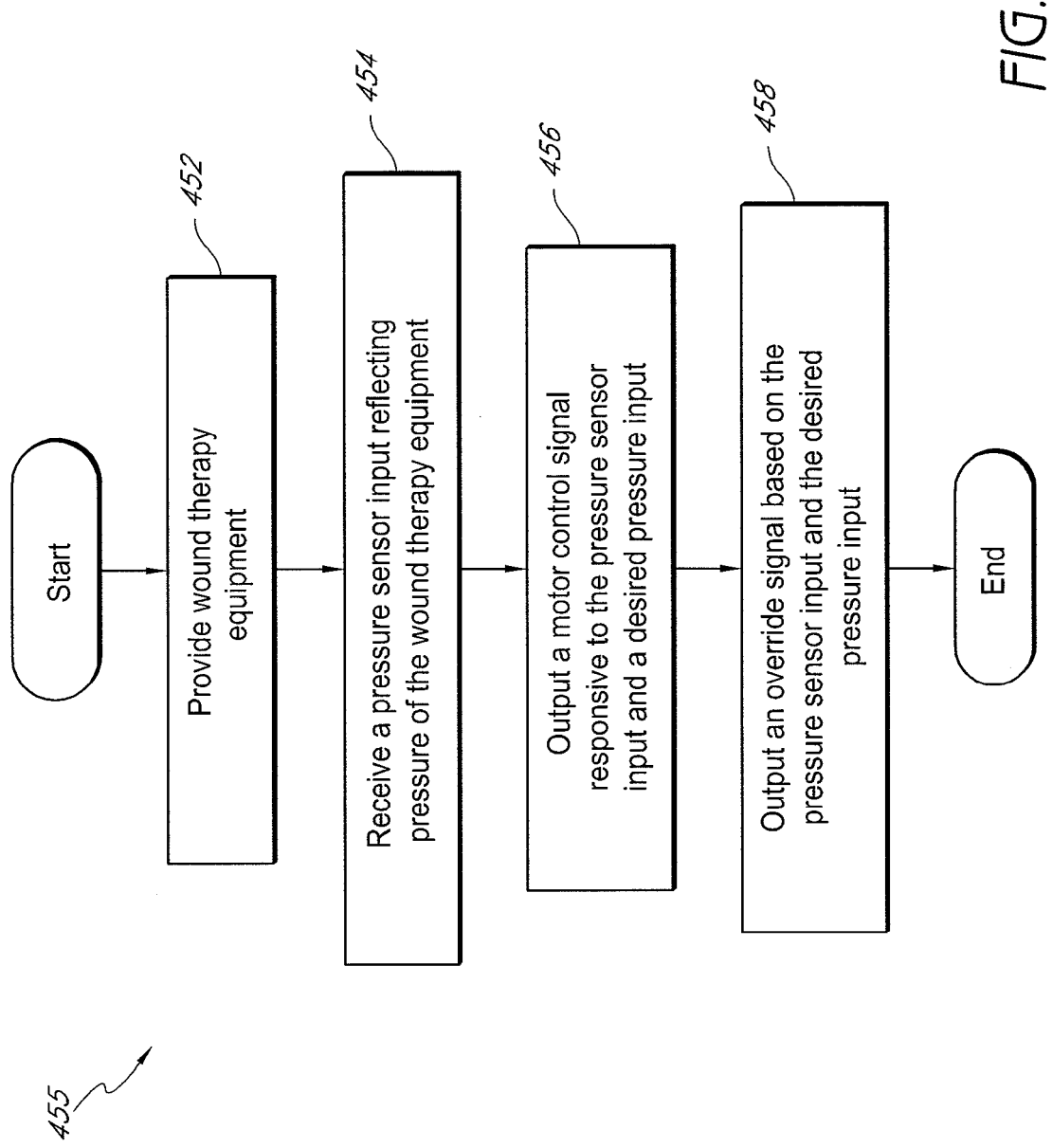
FIG. 12B is an embodiment of a process for treating a wound.

FIG. 12B illustrates an embodiment of a process 450 for treating a wound. The process 450 can be implemented in certain embodiments by any of the NPWT systems described above, including any of the pressure control systems described above. Advantageously, the process 450 can therefore be implemented without using a processor.

At block 452, the process begins by providing wound therapy equipment. This equipment can include, for example, a wound dressing, a fluid collection container, a vacuum pump, and a pressure sensor. The pressure sensor can measure a pressure in the tubing of the vacuum pump, the wound bed, or the like. In certain embodiments, one or more conduits or tubes in the tubing of the vacuum pump channel a flow of fluid between the wound dressing, the fluid collection canister, and the pump.

Continuing, at block 454 the process 450 receives a pressure sensor input from the pressure sensor. This pressure sensor input can reflect the pressure of the wound therapy equipment. The pressure can be the pressure inside the tubing, at the wound bed, or the like. At block 456, the process 450 outputs a motor control signal responsive to the pressure sensor input and a desired pressure input. The motor control signal is operative to control the speed of one or more pump motors. The desired pressure input can be provided, for example, by a user through an input device such as a knob, button, or the like.

The process 450 also outputs an override signal at 450. This override signal can be based at least in part on the pressure sensor input and the desired pressure input. For example, the override signal could be based on a difference between these inputs. In certain embodiments, this difference is an error signal. As described above, as the error is reduced, the override signal can be provided to prevent the motor from stalling.

Advantageously, the process 450 enables a medical patient's wound to be treated more effectively and safely than can be done with currently available vacuum pump devices.

Figure 13:
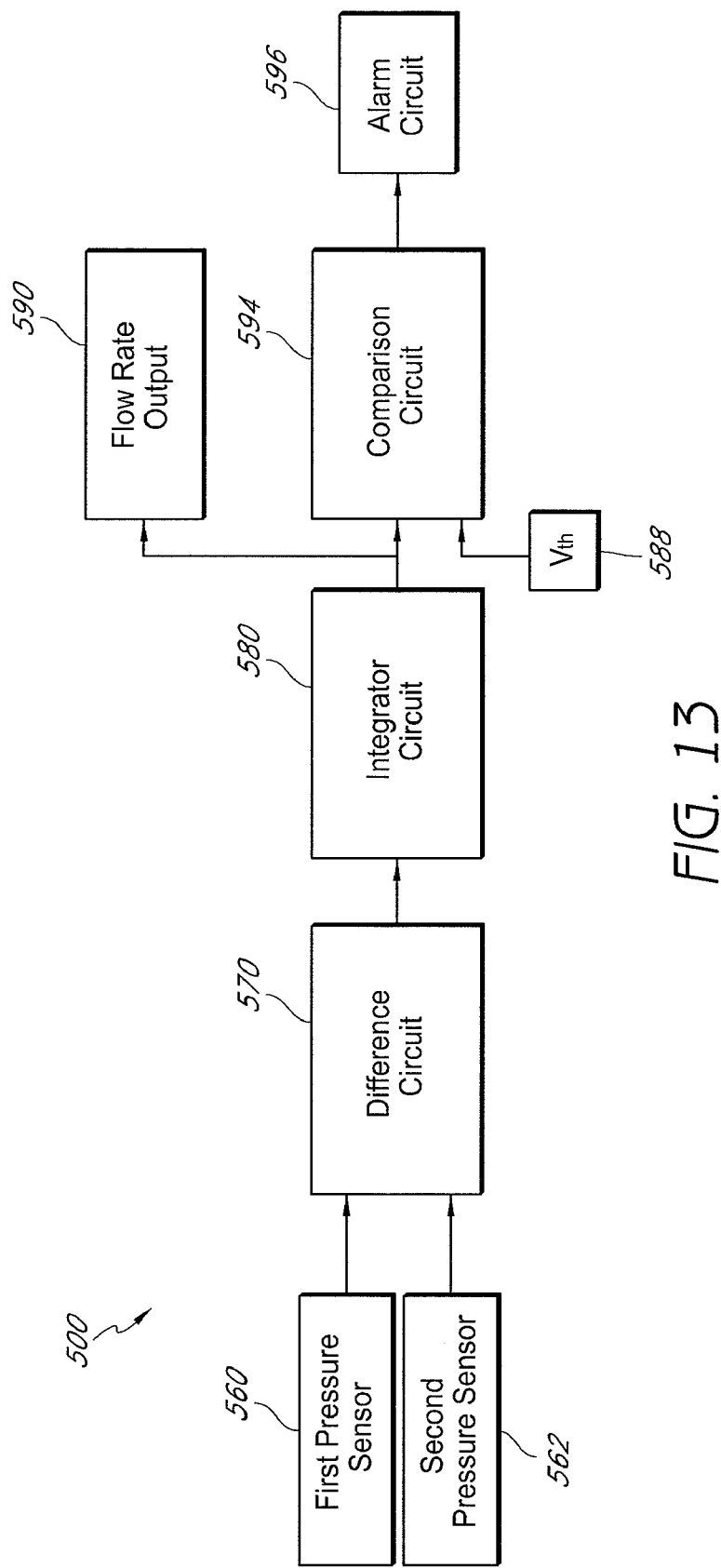
FIG. 13 is a block diagram of an embodiment of a high flow detection and alarm circuit.

FIG. 13 illustrates an embodiment of a high flow detection circuit 500. The high flow detection circuit 500 of certain embodiments can detect potential leaks in a vacuum pump system used for NPWT. The high flow detection circuit 500 can, in various embodiments, provide a measurement of the flow of air and/or an alarm that alerts clinicians to the leak condition.

In various embodiments, the high flow detection circuit 500 includes first and second pressure sensors 560, 562. One or more of the pressure sensors 560, 562 can be similar to the pressure sensor described above. Moreover, in certain embodiments, one or more of the pressure sensors 560, 562 can also be used as a pressure sensor in a pressure control system, such as any of the pressure control systems described above.

The pressure sensors 560, 562 can be connected by a flow restrictor or the like as described above to facilitate determining air flow. In a non-leak condition, in one embodiment little or no air is moving through the tubing. Thus, each of the pressure sensors 560, 562 can measure the same or substantially the same pressure level. However, if a leak occurs, air moving through the flow restrictor can create a pressure difference between the sensors 560, 562.

In an embodiment, a difference circuit 570 is provided for measuring this pressure difference. The difference circuit 570 can be an amplifier, such as an operational amplifier or the like. In addition, the difference circuit 570 can be a comparator. Many other implementations may be chosen, an example of which is shown and described with respect to FIG. 9. The difference circuit 570 outputs a difference signal.

The difference circuit 570 provides the difference signal to the integrator circuit 580. In one embodiment, however, the difference circuit 570 first provides the difference signal to a low pass filter (not shown) for reducing noise in the difference signal, which in turn provides the difference signal to the integrator circuit 580. In certain embodiments, the integrator circuit 580 is also a low pass filter or the like that integrates the difference signal using, for example, one or more capacitors and resistors. By integrating the difference signal, the integrator circuit 580 provides a delay that can prevent the comparison circuit 590 from rapidly switching an alarm on and off.

The integrator circuit 580 in one embodiment provides a flow rate signal as a flow rate output 590. In certain embodiments, the flow rate is proportional to the pressure differential between the two signals, as measured by the difference signal. The flow rate output 590 can be provided to a gauge, digital display, or the like. The flow rate output 590 can also be provided earlier in the high flow detection circuit 590, for example, after the difference circuit or after a low pass circuit (not shown). In addition to, or in place of providing the flow rate signal to the flow rate output 590, the integrator circuit 580 can provide the flow rate signal to a comparison circuit 594. In certain embodiments, the comparison circuit 594 compares the flow rate signal to a threshold voltage 588, $V_{th}$. If the flow rate signal exceeds the threshold voltage 588, in certain embodiments a leak is detected.

The comparison circuit 594 can in turn provide an alarm signal to an alarm circuit 596 in the event of detecting a leak. The alarm circuit can alert a clinician using, for example, audible and/or visual alarms. Thus, the clinician can take corrective action to repair the leak.

Figures 2, 14:
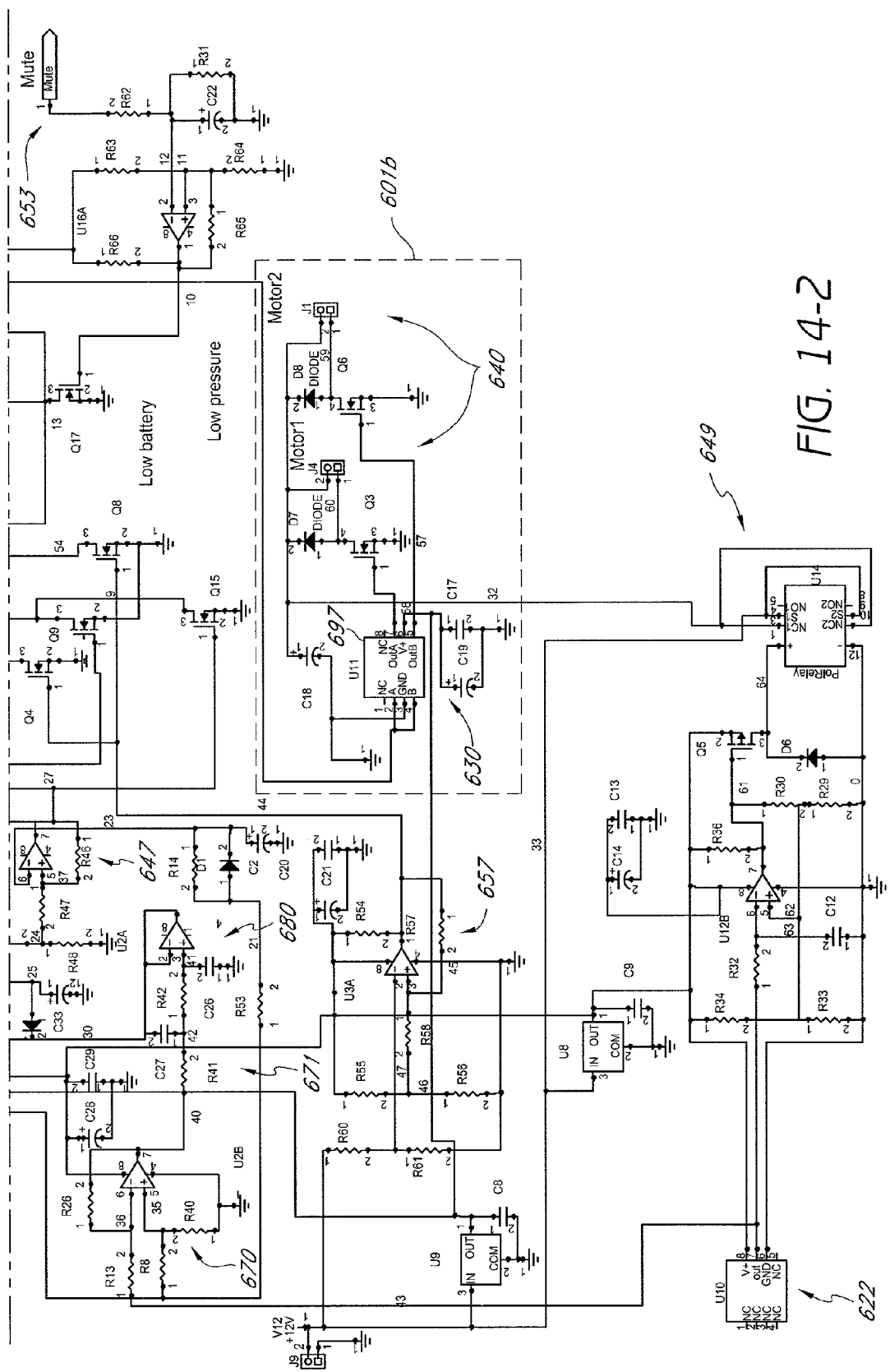
FIG. 14 is a block diagram of an embodiment of a negative wound pressure therapy system.

FIG. 14 illustrates an embodiment of a vacuum pump circuit 600. The vacuum pump circuit 600 includes a pressure control circuit 601 along with several other exemplary circuits useful for vacuum wound pressure therapy. In the depicted embodiment, no processor is used, thereby facilitating one or more of the benefits described above. In addition, two pump motors 640 are provided, facilitating further fault protection and increased suction.

Some or all of the voltage values described herein can vary based on the type, manufacturer, and/or part number of the pressure sensors used. Additionally, the voltage values can vary based on the particular type, manufacturer, and/or part numbers of the resistors, capacitors, diodes, transistors, integrated circuit components, combinations of the same, or the like that are used. Thus, other voltage values than those described herein can result from the choice of various sensors and/or components in various embodiments, without departing from the scope of the embodiments described herein.

The pressure control circuit 601 as shown includes pressure control circuits 601*a* and 601*b*. The pressure control circuit 601*a* includes a pressure sensor 602 and a desired pressure setting provided by an encoder input 604. Like the pressure sensors and desired pressure settings described above, the pressure sensor 602 and the encoder input 604 provide voltage signals to a pressure control circuit having an amplifier 610 (the op amp U4A) and a pulse width modulator 614. In the depicted embodiment, the pulse width modulator 612 includes a comparator U13B, a capacitor C1, and resistors, which together generate a variable duty cycle square wave.

The amplifier 610 and the pulse width modulator 614 both provide outputs to a stall control circuit, which includes a voltage reference 622, a comparison circuit 624, and override logic 626. In the depicted embodiment, the voltage reference 622 is generated by using a resistive divider using resistors R9 and R12 to lower a 5 volt input to about 1.2 volts. The comparison circuit 624 includes a comparator U13A and associated resistors. The override logic includes an AND gate U7A.

In an embodiment, the comparison circuit 624 generates a high logic or voltage value in response to an input signal greater than about 1.26 volts and generates a low logic or voltage value in response to an input signal lower than about 1.06 volts. Between about 1.06 and 1.26 volts, the comparison circuit 624 does not change its output. Thus, the comparison circuit 624 of certain embodiments employs hysteresis, as discussed above.

In certain embodiments, the operation of the pressure control circuit 601 is as follows. The pressure in the vacuum tubing at startup of the circuit is zero or substantially zero, which is much lower than the encoder input 604. Therefore, a difference signal between the pressure sensor input 602 and the encoder input 604 is greater than 1.26V, causing the comparison circuit 624 to output high, allowing the output of the pulse width modulator 614 to reach the pump motors 640.

The duty cycle of the pulse width modulator 614 can be determined by the magnitude of the difference signal, starting at about 100% and decreasing to about 40% as the pressure nears the encoder input 604. The pressure continues to increase and eventually rises past the encoder input 604 by a few millimeters (mmHg), causing the difference signal to fall below 1.06V. This in turn causes the comparison circuit 624 output to go low, cutting power to the pump motors 640. The pressure then slowly falls below the encoder input 604 by a few mmHg, causing the difference signal to rise above 1.26V, in turn causing the comparison circuit 624 to output high. This high output once again allows the pulse width modulator 614 to apply power the pump motors 640. This cycle can continue indefinitely (e.g., until the pump is turned off by a user or the like), maintaining the pressure at the encoder input 604 value within a few mmHg by occasionally pulsing the pump motors 640 with short bursts of about 20 kHz square wave at about 40% duty cycle. Example pressure values of when the pump motors 640 can turn on and off are shown below in Table 1.

TABLE 1

| | Comparison Circuit Output | | | | | | | | | | |
|---|---|---|---|---|---|---|---|---|---|---|---|
| Encoder input (mmHg) | 200 | 180 | 160 | 140 | 120 | 100 | 90 | 80 | 70 | 60 | 50 | 40 |
| Pumps ON (mmHg) | 199 | 179 | 159 | 139 | 120 | 100 | 90 | 80 | 70 | 60 | 50 | 40 |
| Pumps OFF (mmHg) | 201 | 182 | 162 | 142 | 122 | 102 | 92 | 82 | 72 | 62 | 52 | 42 |

The pulse width modulator 614 of certain embodiments does not have a fixed operating frequency. Instead, its frequency can vary with duty cycle, in a fixed, bell shaped relationship. Frequency can peak near 50% at about 25 kHz, dropping to about 8 kHz at 9% and 90% duty cycle.

In certain embodiments, the output to a motor driver circuit 630 is logically ANDed at AND gate U7B with a pump soft-start circuit 651, which is shown as part of the pressure control circuit 601. The motor driver circuit 630 can include an integrated circuit 697 including one or more transistor (e.g., power MOSFET) drivers, discrete transistor drivers, supporting passive component circuitry, combinations of the same, or the like. In alternative embodiments, the pump soft-start circuit 651 is not included with the pressure control circuit 601. The pump soft-start circuit 651 helps ensure that the pump motors 640 do not draw too much current at power on to avoid the protection circuitry in the power supply shutting down the power supply. This circuit is described in further detail below.

In addition to the pressure control circuit 601, a depicted flow rate detection circuit is provided that includes first and second pressure sensors 602, 662, a difference circuit 670, an integrator circuit 680, a comparison circuit 694, and an alarm circuit 696. In an embodiment, the pressure sensor 602 used for pump control is also used for flow rate detection. In addition, a second, backup sensor 662 is also used. In one embodiment, these sensors 602, 662 are both connected to the same general area of the pump plumbing, but spaced slightly apart so that they will measure slightly different pressures as air flows through the plumbing. During normal operation, flow can be so small that there is almost no pressure difference between the sensors. If the suction load were removed, the pumps can run full speed and the flow of air through the plumbing could be much larger.

The difference between the sensors 602, 662 is amplified by a gain of 20 at the difference circuit 670, low pass filtered by a low pass filter 671, and then fed to the integrator circuit 680, which has a 66 second time constant. The integrator circuit 680 output goes to a comparison circuit 694 with a fixed threshold of 1.56 volts in the depicted embodiment. The output of the comparison circuit 694 is provided to the alarm circuit 696, which drives various transistors (e.g., MOSFETs) to turn on a piezoelectric beeper or the like and lights (e.g., light-emitting diodes). In one embodiment, the alarm triggers at a differential pressure of 5 mmHg. The alarm circuit 696 activates in one embodiment at flows greater than about 6 lpm (liters per minute).

In addition to the above circuits, a low pressure alarm circuit of certain embodiments is provided that includes a comparison circuit 647. The comparison circuit 647 includes a comparator U3B that receives the encoder input 604 and the pressure sensor input 602. The low pressure alarm circuitry compares the pressure sensor input 602 to one half of the encoder input 604 voltage. If the pressure sensor input 602 is lower than one half the encoder input 604 voltage for a significant amount of time, an alarm in the alarm circuit 696 turns on. The alarm of the alarm circuit 696 can be turned off much faster than it can be turned on in one implementation, due to the asymmetrical time constant of an integrator including a resistor R14 and a capacitor C2, which filters the pressure sensor input 602. In other embodiments, a value other than one half is used by the comparison circuit 647.

During normal operation, when the pressure sensor input 602 has stabilized at the encoder input 604 the user has selected, the integrator, using a resistor R14 and capacitor C2, charges up to the pressure sensor input 602 voltage in less than one second through resistor R53 and diode D1. If the suction load were to be suddenly removed and the pressure sensor input 602 dropped to zero, the integrator would slowly discharge through resistors R14 and R53. It could take up to 3 minutes in one embodiment for the integrator to discharge to less than one half of the encoder input 604 voltage, which would cause the comparison circuit 647 to output high and turn on the alarm.

The integrator time constant while charging, equal in one embodiment to the value of resistor R14 times capacitor C2, is 0.22 seconds until the pressure sensor input 602 is less than about one diode drop across diode D1 greater than the integrator voltage, when it becomes 66 seconds. This difference occurs because diode D1 stops conducting when the voltage across it is less than about one diode drop.

Example times it can take to turn the alarm on, listed in Table 2 below, assumes the pressure sensor input 602 has been stable at the indicated encoder input 604 value for several minutes, and that the pressure goes to zero nearly instantly. These assumptions may not apply or may be different in some embodiments.

TABLE 2

Low pressure alarm activation pressures and time to activate

| knob (mmHg) | alarm ON (mmHg) | alarm OFF (mmHg) | Time to alarm on from encoder input value to zero pressure (in seconds) |
|---|---|---|---|
| 200 | 76 | 82 | 64 |
| 180 | 69 | 71 | 64 |
| 160 | 61 | 65 | 66 |
| 140 | 50 | 55 | 68 |
| 120 | 42 | 46 | 70 |
| 100 | 33 | 37 | 74 |
| 90 | 28 | 32 | 77 |
| 80 | 24 | 28 | 80 |
| 70 | 19 | 24 | 84 |
| 60 | 15 | 20 | 91 |
| 50 | 10 | 14 | 102 |
| 40 | 7 | 11 | 124 |

Another circuit, a high pressure cutoff circuit, can also be provided. The high pressure cutoff circuit includes a comparison circuit 649, which in turn includes a comparator U12B. The comparison circuit 649 can remove electrical power from both pump motors 640 when the pressure from the second, backup pressure sensor 662 is higher than a fixed threshold. This circuit 649 can override all other pump power control because pump power is routed directly through a relay U14 that overrides the pump motors 640. The voltage from the second pressure sensor 662 can be low pass filtered by resistor R32 and capacitor C12. When the second pressure sensor 662 input reaches or exceeds 217 mmHg, power is removed from both pump motors 640 and does not return until the second pressure sensor 662 input falls below 212 mmHg. The comparator U12B of certain embodiments is active-low. When high, it turns on the relay U14 and allows power to reach the pump motors 640. When low, the relay U14 is turned off and power is disconnected from the pump motors 640.

In certain embodiments the high pressure cutoff circuit can be used as a redundant safety feature. Thus, the high pressure cutoff circuit may cut power to the pump motors 640 only when one or more components in the vacuum pump circuit 600 fails. Thus, for example, if a transistor or op amp in the pressure control circuit 601 fails, the high pressure cutoff circuit can cut power to the pump motors 640.

An intermittent delay circuit 645 is also provided that can change the overall duty cycle of the entire suction pump motors 640 from about 100% to about 60%, or to another desired percentage. The intermittent delay circuit 645 can accomplish this by periodically shorting the encoder input 604 wiper to ground, effectively telling the pressure control circuit 601 that the desired pressure is zero. After a delay of about 16 seconds, the wiper is released from ground, returning to whatever input value the user has selected for a delay of about 32 seconds. This cycle can repeat indefinitely as long as intermittent mode is selected. Other values for the delay values can be selected.

In one embodiment, the resistors R37 and R38 and the capacitor C23 set the on time ($T_{on}$) and off time ($T_{off}$) of the intermittent circuit 645, according to the following expressions:

$$T_{on} = 0.693(R37+R38)*C23 \qquad (2)$$

$$T_{off} = 0.693(R38)*C23. \qquad (3)$$

In certain embodiments, a pump soft start circuit 651 is also provided that prevents the pump motors 640 from running at 100% duty cycle during power up, since 100% duty cycle could draw significant current from the power supply, which could cause the power supply to enter overcurrent shutdown.

At startup, a capacitor C5 of the pump soft start circuit 651 is discharged. This can mean that the gate of transistor Q2 is 5 volts, which can mean that transistor Q2 is turned on, which in turn shunts the comparator U13B of the pulse width modulator 614 to ground through three diode drops. At this point, the pulse width modulator 614 input can be limited to three diode drops above ground (e.g., common), which effectively prevents the pulse width modulator 614 from outputting a high duty cycle to the pump motors 640. As capacitor C5 charges, the voltage across it increases, which means the voltage at the gate of the transistor Q2 continues to fall until the transistor Q2 turns off, removing the limit from the input of the pulse width modulator 614. The limit remains in effect for about 500 ms (milliseconds) in one embodiment.

Additionally, a mute circuit 653 is provided to allow the user to silence the audible alarm circuit 696 for a preset, fixed amount of time. The output of the mute circuit 653 controls transistor Q17, which controls U6, which is a 555 timer that controls the piezoelectric buzzer. When the output of the mute circuit 653 is 5 volts, the transistor Q17 is turned on, which enables the 555 timer U6 to be turned on by an alarm. This in turn means that the buzzer can turn on. When the output of the mute circuit 653 is 0 volts, the transistor Q17 is off and no power can reach the 555 timer U6. As a result, no power can reach the buzzer.

A mute button can be provided on the front panel of the vacuum pump, which can be a momentary switch or the like. The switch can connect 5 volts to resistor R62 when depressed. Activating the switch charges up capacitor C22 to 5 volts in about 100 ms. When the mute button is released, the capacitor C22 slowly discharges through the resistor R31. The comparator U16 compares the voltage across the capacitor C22 to a threshold of 1.47 volts, provided by a voltage divider of resistors R64 and R63.

The time the mute circuit 653 remains active is controlled by the voltage divider R64 and R63, by the capacitor C22, and by the resistor R31. In one embodiment, the values of the capacitor C22 and the resistor R31 can be chosen so that the mute time can be set from between 0 and 354 seconds by varying the resistors R64 and R63, e.g., by using user-controlled potentiometers for the resistors R64, R63. The time the mute function remains active can be expressed as:

$$t = R31*C22*\ln(5/V_{div}), \qquad (4)$$

where $V_{div}$ is the voltage of the R64/R63 voltage divider.

Moreover, a low voltage alarm circuit 657 can be provided that activates when the +12 volt supply, either from a battery, AC adapter, or DC in jack, falls below about 10V. It can include a simple comparator U3A which compares one fourth of the +12 voltage rail to a fixed threshold of 2.5 volts. The output is active at 5 volts and drives transistors (e.g., MOSFETs) which control the beeper and alarm circuit 696.

Based on the foregoing description, one can see that providing pressure control without using a processor provides significant advantages over existing systems. In particular, reduced cost, increased safety, and a less-complex FDA approval process are some advantages provided by certain embodiments described herein.

In addition to the components and features described herein, any of the embodiments of the NPWT apparatus described herein can have any of the features and components that are known in the art or that are suitable for such system. The EZCARE Negative Pressure System User Guide available from Smith & Nephew is hereby incorporated by reference as if fully set forth herein. The pressure control circuitry described herein can be configured to be used with any NPWT apparatus currently available or later developed. Additionally, the disclosure set forth in PRESSURE CONTROL OF A MEDICAL VACUUM PUMP, International Application No. PCT/US2007/021790, filed in the PCT, and designating the United States, on Oct. 12, 2007, is hereby incorporated by reference as if fully set forth herein.

With reference to FIGS. 15-18, additional embodiments of NPWT apparatuses will be described. The additional embodiments of NPWT apparatuses illustrated in FIGS. 15-18 may be suitable for use with, but not limited to, mechanically derived power sources and/or electric power generators. NPWT apparatuses utilizing mechanically derived power sources may comprise a mechanical clockwork drive or a clockwork driven dynamo power source to power the NPWT vacuum related components. In a very basic form, a syringe type device of the type described in U.S. Pat. No. 3,841,331, the entirety of which is hereby incorporated by reference, may be directly powered by a mechanical clockwork drive arrangement to cause the piston and piston stem to be reciprocated in a cylinder to provide negative or positive pressure at a wound site.

In some embodiments utilizing mechanically derived power, a mechanically driven gas compressor may charge an accumulator to a relatively high pressure, which acts through a system controller to pneumatically drive a pump by gas pressure. Although a pump driven by a vacuum or negative pressure could be used, a positive pressure system would give longer periods of operation in comparison to a vacuum drive based system. A positive pressure accumulator can easily achieve up to ten atmospheres of pressure or more, whereas vacuum systems can generally achieve, at best, up to one atmosphere of pressure below the ambient pressure.

Figure 15:
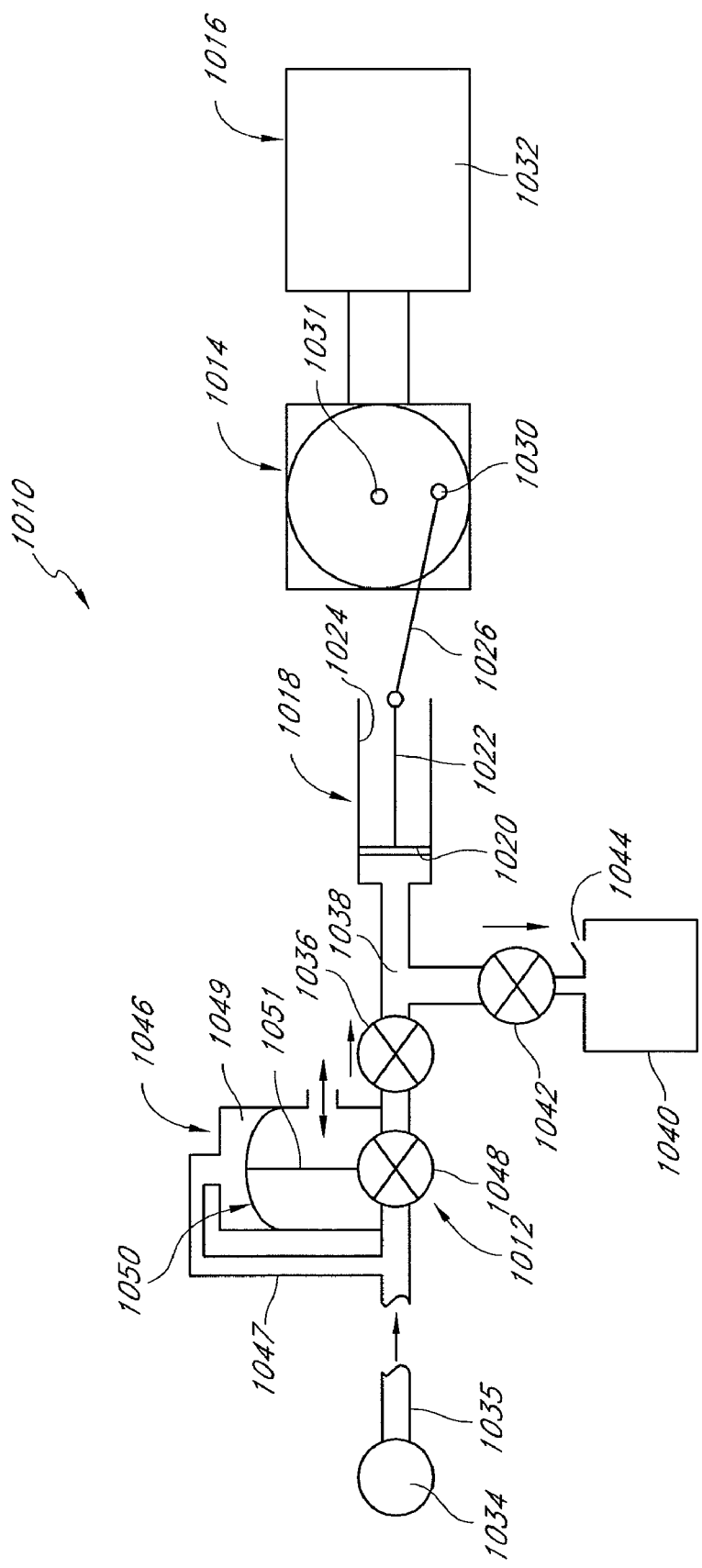
FIG. 15 is a schematic representation of another embodiment of a negative pressure wound therapy apparatus.

FIG. 15 is a schematic representation of another embodiment of an NPWT apparatus. In the illustrated embodiment, the NPWT apparatus 1010 preferably comprises a suction/negative pressure or positive pressure unit 1012, a drive unit 1014, and an accumulator unit 1016 to provide motive power to the drive unit 1014. The pressure unit 1012 preferably comprises a syringe or piston pump 1018 having a piston 1020 and piston rod 1022 moving in a cylindrical bore 1024. The piston 1020 and piston rod 1022 are preferably configured to reciprocate within the cylindrical bore 1024 by means of an articulated linkage 1026 which translates rotary motion of an eccentrically located crankpin 1030 about an axis 1031 into linear motion of the piston 1020 and piston rod 1022. The crankpin 1030 is preferably driven by a clockwork device 1032, which can be a mechanical energy accumulator in the form of a wound spring. When the piston 1020 reciprocates, it preferably creates suction or negative pressure at a wound 1034 having a dressing (not shown) in a known manner, thus preferably drawing air and fluid from the wound site 1034 through a conduit 1035 from the wound site dressing then through a first one-way valve 1036 when the piston 1020 is moving in a left to right direction, as shown in FIG. 15. By maintaining the mechanical accumulator unit in a wound condition, the suction/pressure unit 1012 and the drive unit 1014 may be kept operative indefinitely without recourse to AC power.

When the piston 1020 moves back in a right to left direction, as driven by rotation of the crankpin 1030, air and fluid trapped in the space 1038 is expelled into a waste container 1040 through a second one-way valve 1042, preferably causing the air to escape to the surrounding atmosphere through a vent 1044 in the container 1040. A filter (not shown), which may be a pathogen filter, preferably filters the expelled air to avoid expelling bio-hazardous material to the atmosphere.

In some embodiments, the apparatus 1010 preferably also includes a diaphragm valve 1046 linked to a proportional shut-off valve 1048. A flexible diaphragm 1050 preferably automatically closes the valve 1048 when the pressure at the wound 1034, which is preferably lower than the ambient pressure, reaches a predetermined value. In some embodiments, the value of the negative pressure at the wound site 1034 can be monitored via the conduit 1035 and a conduit branch 1047 to a space 1049 above the diaphragm 1050. The required pressure may be set by manually adjusting a sprung preload 1051 acting on the diaphragm 1050.

In some embodiments, the diaphragm 1050 and space 1049 of the apparatus 1010 may be connected directly to the wound site dressing 1034 via a separate conduit (not shown). In some embodiments, by changing the direction of the one-way valve 1036 and eliminating or closing the second one-way valve 1042, the apparatus may be used to apply positive pressure to the wound site 1034 to administer medicaments, for example.

Figure 16:
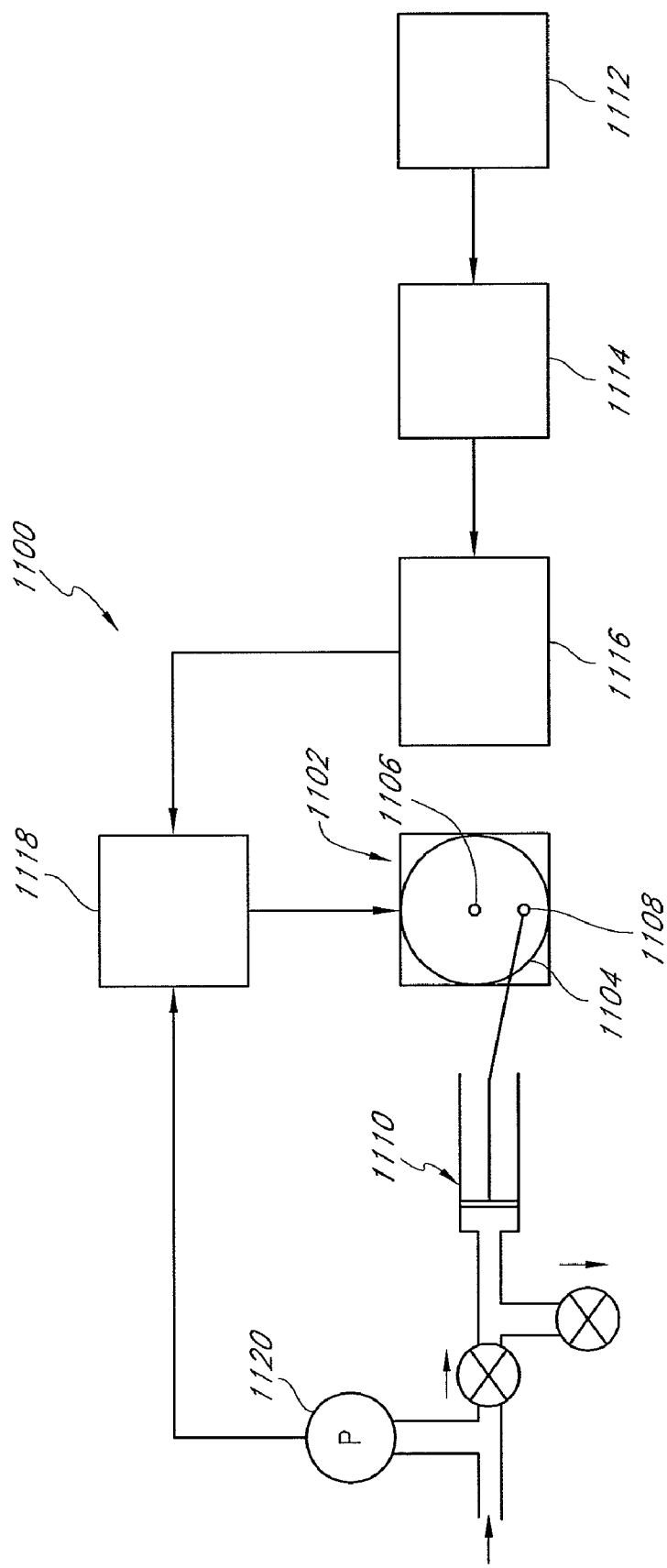
FIG. 16 is a schematic representation of another embodiment of a negative pressure wound therapy apparatus.

FIG. 16 is a schematic representation of another embodiment of an NPWT apparatus. In the illustrated embodiment, the drive unit 1102 may comprise an electric motor 1104 having a rotary shaft rotating about an axis 1106 and having an eccentric crankpin 1108 thereon drivingly linked in a similar manner to a syringe-type pressure/suction device 1110, as is described with respect to the NPWT apparatus 1010 above. In this embodiment, the drive unit 1102 is preferably supplied with electrical current by a dynamo or electrical generator 1112, which delivers current through a charging controller 1114 to a storage battery 1116 and to the drive unit 1102 through a control unit 1118. The control unit 1118 is preferably connected to a pressure sensor 1120, which measures pressure at a wound site (not shown) and provides pressure data to the control unit 1118 which has stored in a memory therein a desired pressure to achieve. When the desired pressure at a wound site is reached, as sensed by the sensor 1120 and conveyed to the control unit 1118, the control unit preferably ceases to supply current to the drive unit 1102 until pressure in the wound site changes beyond the desired value. The drive unit 1102 will then be signaled by the control unit 1118 to start again to maintain the pressure at the wound site within the desired range stored in the memory of the control unit 1118. The dynamo/electrical generator 1112 may be powered by a purely mechanical device such as a clockwork drive or may be powered by a small internal combustion motor, for example.

Figure 17:
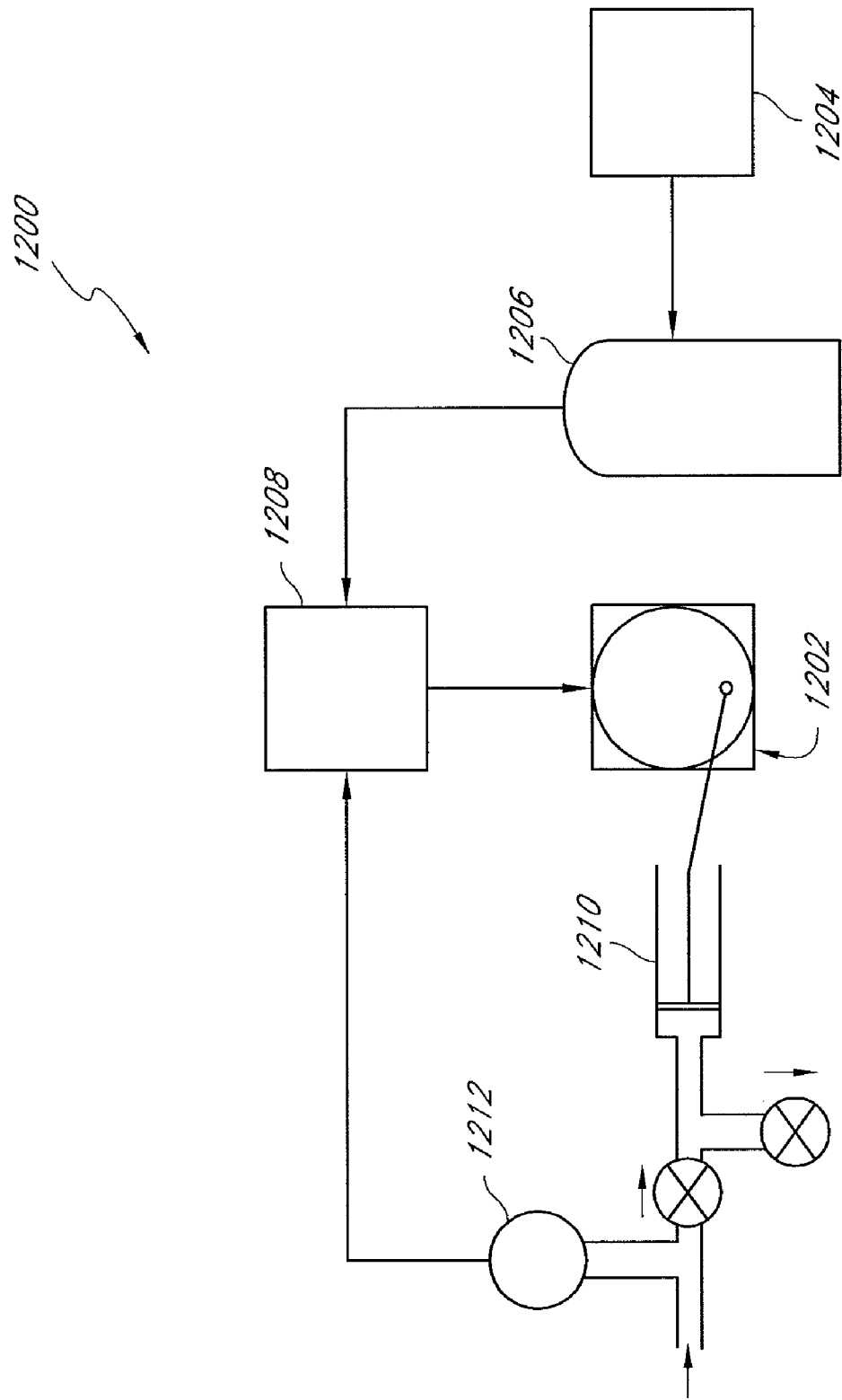
FIG. 17 is a schematic representation of another embodiment of a negative pressure wound therapy apparatus.

FIG. 17 is a schematic representation of another embodiment of an NPWT apparatus. In the illustrated embodiment, the embodiment of the NPWT apparatus illustrated in FIG. 17 is similar to that of FIG. 16, except that the power source to drive the drive unit 1202 is a compressor 1204 which preferably pressurizes an accumulator 1206 with air. The pressurized air is then fed to a pneumatic drive 1202 through a system control unit 1208 to provide motive power to a syringe type suction/pressure unit 1210 as with FIGS. 15 and 16. A pressure sensor 1212 senses pressure at a wound site (not shown) and compares the sensed pressure with a stored desired value in a memory of the system controller 1208. When a desired pressure (negative or positive) is achieved, the controller 1208 ceases to supply pressurized air to the drive unit 1208 and the drive unit stops until the pressure sensed by the sensor 1212 falls outside of preset tolerances stored in the memory of the controller 1208.

Figure 18:
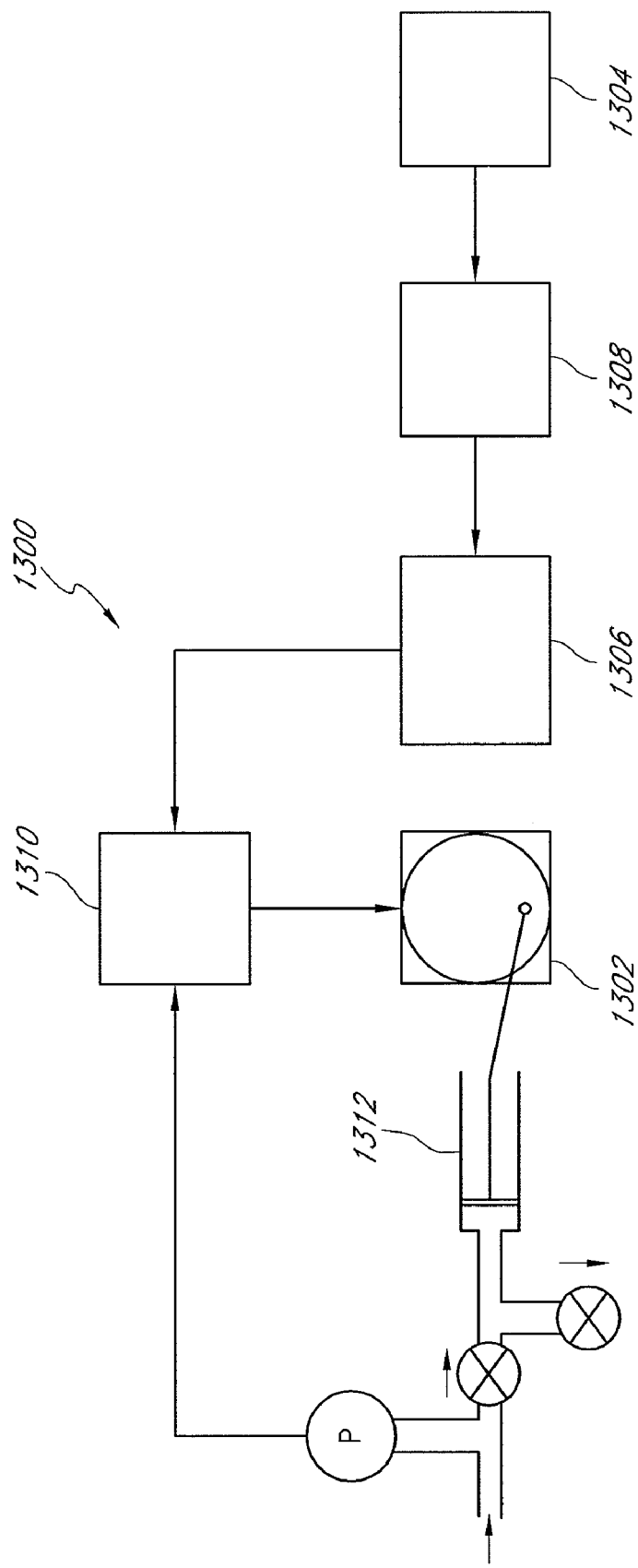
FIG. 18 is a schematic representation of another embodiment of a negative pressure wound therapy apparatus.

FIG. 18 is a schematic representation of another embodiment of an NPWT apparatus. In this embodiment of the NPWT apparatus 1300, the power source that is configured to drive the drive unit 1302 is preferably provided by solar cells 1304 which supply electrical current to charge a battery 1306 through a charging controller 1308. Current from the battery 1306 is fed to the electric motor drive unit 1302 through a system controller 1310 which operates as in the apparatus of FIG. 16 to control movement of the syringe type pump 1312.

The syringes described above may be a preferred choice for inclusion with any of the above-described NPWT apparatuses because they are generally low-cost, readily available, and disposable. However, the NPWT apparatuses described above are not so limited. Any suitable type of pump can be employed, such as, for example, diaphragm pumps, centrifugal pumps, double-acting piston pumps, and multiple piston pumps, without departing from the essence of the disclosure. Thus, it will be appreciated that, in the embodiments of FIGS. 15-18, the power source may be directly connected to the vacuum pump components. The power source may be a purely mechanical device such as a clockwork motor, as in FIG. 15, or may be relatively more complex, as is set forth in the embodiments of FIGS. 16-18. In these embodiments, the NPWT apparatus can function independently of a source of AC current.

While the above detailed description has shown, described, and pointed out novel features as applied to various embodiments, it will be understood that various omissions, substitutions, and changes in the form and details of the device or process illustrated may be made without departing from the spirit of the disclosure. Additionally, the various features and processes described above may be used independently of one another, or may be combined in various ways. All possible combinations and subcombinations are intended to fall within the scope of this disclosure.

As will be recognized, certain embodiments described herein may be embodied within a form that does not provide all of the features and benefits set forth herein, as some features may be used or practiced separately from others. The scope of the inventions is indicated by the appended claims rather than by the foregoing description. All changes which come within the meaning and range of equivalency of the claims are to be embraced within their scope.

What is claimed is:

1. A negative pressure wound therapy apparatus, comprising:
   a vacuum pump comprising a pump motor connectable to a primary power source selected from the group consisting of photovoltaic power and human power, the vacuum pump operatively coupleable to a wound dressing and configured to selectively draw a fluid from the wound dressing;
   an auxiliary power source operatively coupleable to the pump motor, wherein the auxiliary power source comprises an auxiliary power module configured to selectively supply supplemental power to the pump motor for powering the pump motor, wherein the auxiliary power module is portable and not an AC power source; and
   a power controller configured to augment the power provided by the primary power source with supplemental power from the auxiliary power source when the power provided by the primary power source is insufficient to power the vacuum pump.

2. The apparatus of claim 1, further comprising a wound dressing removably positionable over a wound.

3. The apparatus of claim 2, further comprising a canister suitable for containing fluid configured to be interposed between the vacuum pump and the wound dressing.

4. The apparatus of claim 1, wherein the auxiliary power module is a fuel cell.

5. The apparatus of claim 1, wherein the auxiliary power module is a generator.

6. The apparatus of claim 5, wherein the generator is combustion powered.

7. The apparatus of claim 1, wherein the auxiliary power module is a battery.

8. The apparatus of claim 1, wherein the auxiliary power module is a mechanical accumulator.

9. The apparatus of claim 1, wherein the photovoltaic power source comprises a photovoltaic panel.

10. A method of providing power to the negative pressure wound therapy apparatus of claim 1.

11. The apparatus of claim 1, wherein the auxiliary power module is configured to selectively supply auxiliary power from a second auxiliary power module.

12. The apparatus of claim 1, wherein the power controller is configured to serve as a switch between the provision of power from either just the primary power source, the primary power source and the auxiliary power source, or just the auxiliary power source.

13. A negative pressure wound therapy apparatus, comprising:
    a vacuum pump comprising a pump motor connectable to a primary power source selected from the group consisting of photovoltaic power and human power, the vacuum pump operatively coupleable to a wound dressing and configured to selectively draw a fluid from the wound dressing;
    an auxiliary power source operatively coupleable to the pump motor, wherein the auxiliary power source comprises an auxiliary power module configured to selectively supply supplemental power to the pump motor for powering the pump motor, wherein the auxiliary power module is portable and not an AC power source, wherein the auxiliary power source is a battery; and
    a power controller, wherein the power controller is configured to direct power from the primary power source to the battery when the power provided by the primary power source is above the amount needed by the vacuum pump.

14. The apparatus of claim 13, further comprising a wound dressing removably positionable over a wound.

15. The apparatus of claim 14, further comprising a canister suitable for containing fluid configured to be interposed between the vacuum pump and the wound dressing.

16. The apparatus of claim 13, wherein the photovoltaic power source comprises a photovoltaic panel.

17. The apparatus of claim 13, wherein the power controller is configured to serve as a switch between the provision of power from either just the primary power source, the primary power source and the auxiliary power source, or just the auxiliary power source.

* * * * *